(12) United States Patent
Tschopp et al.

(10) Patent No.: US 12,181,192 B2
(45) Date of Patent: Dec. 31, 2024

(54) METHODS AND DEVICES FOR CONTROLLING THE TEMPERATURE OF A SURFACE

(71) Applicant: Black & Decker, Inc., New Britain, CT (US)

(72) Inventors: Tylan A. Tschopp, Baltimore, MD (US); Lauren Lynch Clayton, Baltimore, MD (US); Ashok Samuel Baskar, Glen Arm, MD (US); Christopher Lee Garbutt, Middlesbrough (GB); Zara Elizabeth Jones, Marriottsville, MD (US); Yen Lim Lee, Penang (MY); Jianquan Li, Foshan (CN); Liangxiong Huang, Xingning (CN); Yunfei Zhong, Foshan (CN); Yamin Jiang, Daye (CN)

(73) Assignee: BLACK & DECKER, INC., New Britain, CT (US)

( * ) Notice: Subject to any disclaimer, the term of this patent is extended or adjusted under 35 U.S.C. 154(b) by 0 days.

(21) Appl. No.: 17/956,710

(22) Filed: Sep. 29, 2022

(65) Prior Publication Data

US 2024/0093927 A1 Mar. 21, 2024

Related U.S. Application Data

(60) Provisional application No. 63/407,577, filed on Sep. 16, 2022.

(51) Int. Cl.
*F25B 49/02* (2006.01)
*A61M 5/142* (2006.01)
*F25B 13/00* (2006.01)

(52) U.S. Cl.
CPC ......... *F25B 49/02* (2013.01); *A61M 5/14212* (2013.01); *F25B 13/00* (2013.01)

(58) Field of Classification Search
CPC .................. F25B 49/02; F25B 13/00
See application file for complete search history.

(56) References Cited

U.S. PATENT DOCUMENTS 4,213,292 A * 7/1980 Dolezal .................. H10N 10/00
368/204
4,930,317 A * 6/1990 Klein ........................ A61F 7/00
62/3.5

(Continued)

FOREIGN PATENT DOCUMENTS

DE 202011108636 U1 3/2013
JP 3220810 B2 10/2001

(Continued)

*Primary Examiner* — Henry T Crenshaw
(74) *Attorney, Agent, or Firm* — Caeden Curtis Drayton

(57) ABSTRACT

Disclosed herein are systems and methods for a method for controlling the temperature of a surface. In some embodiments, the method includes applying a variable input to a heat pump (e.g., a Peltier) in thermal communication with the surface. The variable input may vary about a voltage and may include a powered period and an unpowered period. In some embodiments, the method includes measuring a temperature of an element in thermal communication with the surface, determining, based on the temperature of the element, whether a temperature of the surface is within a safe temperature range for a user in thermal communication with the surface, in response to determining the surface is not within the safe temperature range, adjusting the voltage of the variable input to the heat pump, and in response to determining the surface is within the safe temperature range, continuing operation of the variable input at the voltage.

10 Claims, 32 Drawing Sheets

(56) References Cited

U.S. PATENT DOCUMENTS

| | | |
|---|---|---|
| 5,146,765 A | 9/1992 | Waters |
| 5,255,520 A * | 10/1993 | O'Geary ............... F25B 21/02 |
| | | 62/3.2 |
| 5,287,513 A | 2/1994 | Ferguson |
| 5,564,124 A | 10/1996 | Elsherif et al. |
| 5,802,865 A | 9/1998 | Strauss |
| 6,192,702 B1 | 2/2001 | Shimogori |
| 6,217,294 B1 | 4/2001 | Amieri et al. |
| 6,543,247 B2 | 4/2003 | Strauss |
| 6,915,641 B2 | 7/2005 | Harvie |
| 7,331,183 B2 | 2/2008 | Askew |
| 7,828,524 B2 | 11/2010 | Chen |
| 7,892,306 B2 | 2/2011 | Kummer et al. |
| 8,087,254 B2 | 1/2012 | Arnold |
| 8,696,300 B1 | 4/2014 | Burke, Jr. et al. |
| 9,339,066 B2 | 5/2016 | Codner et al. |
| 9,420,082 B2 | 8/2016 | Park et al. |
| 9,794,683 B2 | 10/2017 | Kim |
| 9,851,113 B2 | 12/2017 | Clemente |
| 9,985,596 B1 | 5/2018 | Litovsky et al. |
| 10,024,679 B2 | 7/2018 | Moore et al. |
| 10,129,647 B2 | 11/2018 | Seo et al. |
| 10,182,937 B2 | 1/2019 | Smith et al. |
| D841,796 S | 2/2019 | Freeland et al. |
| 10,443,865 B1 | 10/2019 | Karniol |
| 10,540,138 B2 | 1/2020 | Nahman et al. |
| 10,570,920 B2 | 2/2020 | Lee |
| 10,582,301 B2 | 3/2020 | Hatta |
| 10,704,564 B2 | 7/2020 | Jones |
| 10,709,601 B2 | 7/2020 | Adair |
| 10,765,166 B2 | 9/2020 | Krishnan |
| 11,256,309 B2 | 2/2022 | Smith et al. |
| 2002/0069906 A1 * | 6/2002 | Macris ............... H10N 10/01 |
| | | 136/203 |
| 2005/0000231 A1 * | 1/2005 | Lee ............... F25B 21/04 |
| | | 62/3.5 |
| 2006/0195168 A1 * | 8/2006 | Dunbar ............... A61N 1/36021 |
| | | 607/108 |
| 2007/0299489 A1 | 12/2007 | Francis, Jr. et al. |
| 2009/0312676 A1 * | 12/2009 | Rousso ............... A61F 7/10 |
| | | 607/113 |
| 2010/0198322 A1 | 8/2010 | Joseph et al. |
| 2011/0259028 A1 | 10/2011 | Lee |
| 2012/0031582 A1 | 2/2012 | Sullivan |
| 2012/0065716 A1 | 3/2012 | Gill et al. |
| 2014/0316269 A1 * | 10/2014 | Zhang ............... A61B 8/4209 |
| | | 602/1 |
| 2014/0369541 A1 | 12/2014 | Miskin et al. |
| 2016/0205453 A1 | 7/2016 | Wiese et al. |
| 2017/0035602 A1 | 2/2017 | Shapiro et al. |
| 2017/0266038 A1 | 9/2017 | Peavy et al. |
| 2017/0325875 A1 | 11/2017 | Assmus et al. |
| 2018/0042761 A1 | 2/2018 | Smith et al. |
| 2018/0142924 A1 | 5/2018 | Limon |
| 2018/0295901 A1 | 10/2018 | Kittaka et al. |
| 2018/0325199 A1 | 11/2018 | Otey |
| 2019/0110950 A1 | 4/2019 | Smith et al. |
| 2019/0117820 A1 | 4/2019 | Dam |
| 2019/0234412 A1 | 8/2019 | Schwimmer et al. |
| 2019/0320258 A1 | 10/2019 | Ohura |
| 2019/0350279 A1 | 11/2019 | Clemente |
| 2020/0054080 A1 | 2/2020 | Luo |
| 2020/0110047 A1 * | 4/2020 | Hume ............... H05B 3/06 |
| 2020/0187574 A1 | 6/2020 | Te Hsiang |
| 2020/0300256 A1 | 9/2020 | Kennedy |
| 2020/0309152 A1 | 10/2020 | Sanford |
| 2020/0329806 A1 | 10/2020 | Wong |
| 2020/0352777 A1 | 11/2020 | Smith et al. |
| 2022/0096317 A1 | 3/2022 | Smith et al. |

FOREIGN PATENT DOCUMENTS

| | | |
|---|---|---|
| JP | 6423073 B2 | 10/2018 |
| JP | 6598359 B2 | 10/2019 |
| KR | 20120077197 A | 7/2012 |
| KR | 101713497 B1 | 3/2017 |
| KR | 20190020896 A | 3/2019 |
| KR | 101965793 B1 | 4/2019 |
| KR | 101979679 B1 | 8/2019 |
| KR | 20200003835 A | 1/2020 |
| KR | 20200007123 A | 1/2020 |
| KR | 102075691 B1 | 3/2020 |
| KR | 20200058926 A | 5/2020 |
| WO | 2019138782 A1 | 7/2019 |
| WO | 2020091220 A1 | 5/2020 |

* cited by examiner

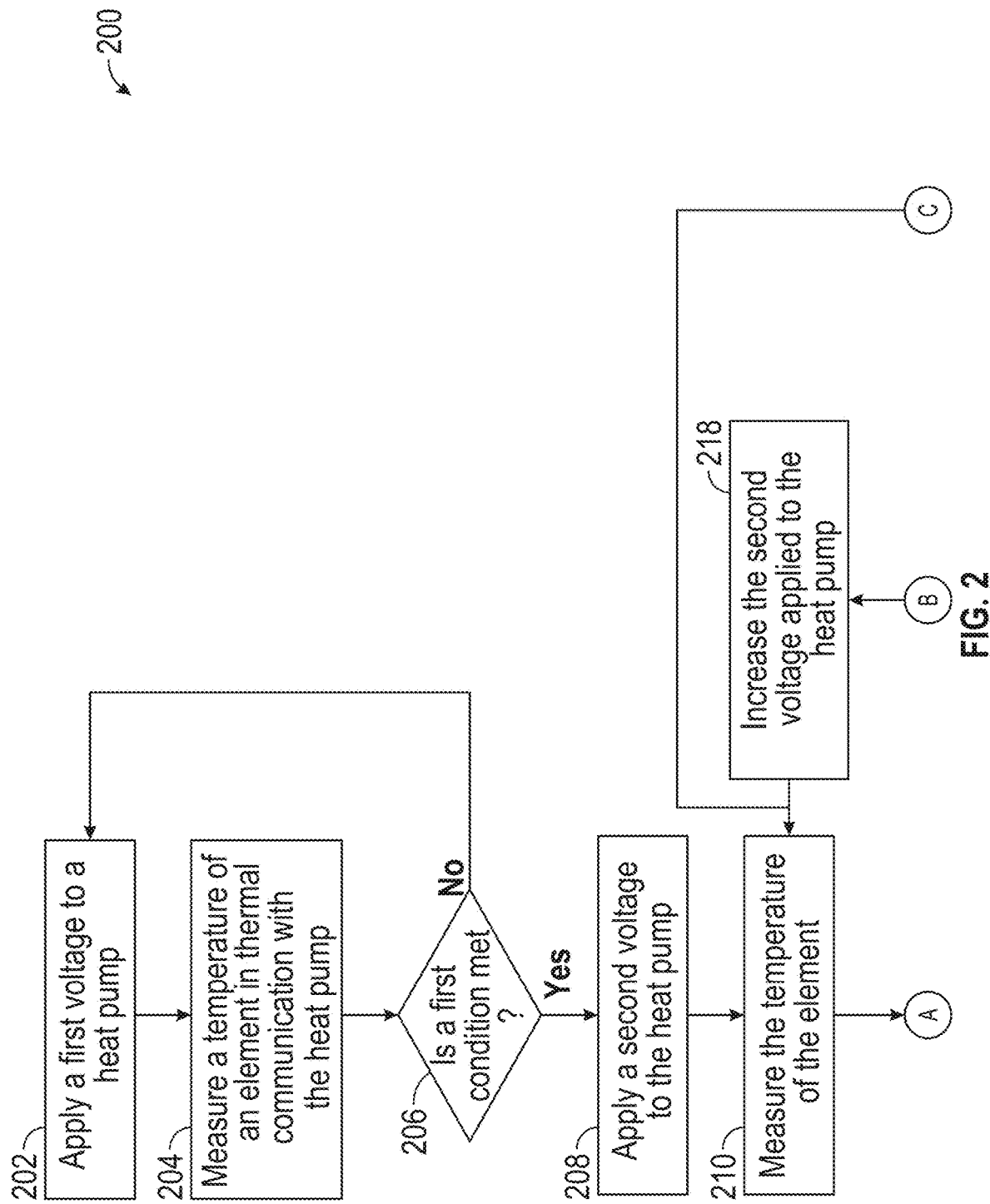

METHODS AND DEVICES FOR CONTROLLING THE TEMPERATURE OF A SURFACE

CROSS REFERENCE TO RELATED APPLICATION

This application claims the benefit of U.S. Provisional Application No. 63/407,577, filed Sep. 16, 2022, the entirety of which is incorporated by reference herein.

FIELD

This disclosure generally relates to a device for controlling the temperature of a surface in thermal communication with a user. More specifically, this disclosure relates to a thermal adjustment device and methods for operating same.

BRIEF SUMMARY

Disclosed herein are systems and methods for controlling the temperature of a surface.

One implementation of the present disclosure is a method for controlling the temperature of a surface. In some embodiments, the method includes applying a variable input to a heat pump (e.g., a Peltier) in thermal communication with the surface. The variable input may vary about a voltage and may include a powered period and an unpowered period. In some embodiments, the method includes measuring a temperature of an element in thermal communication with the surface, determining, based on the temperature of the element, whether a temperature of the surface is within a safe temperature range for a user in thermal communication with the surface, in response to determining the surface is not within the safe temperature range, adjusting the voltage of the variable input to the heat pump (e.g., Peltier), and in response to determining the surface is within the safe temperature range, continuing operation of the variable input at the voltage.

In some embodiments, the safe temperature range for the user is between 10 degrees Centigrade (in some embodiments, 15 degrees) and 49 degrees Centigrade (in some embodiments, 58 degrees or 50 degrees). In some embodiments, a duty cycle of the variable input is at least 10%. In some embodiments, a duration of the powered period is greater than a duration of the unpowered period. In some embodiments, the voltage of the variable input is between 1.7 Volts and 4.0 Volts. In some embodiments, the voltage of the variable input is within a safe operating range for the heat pump. In some embodiments, applying the variable input to the heat pump includes operating the heat pump in two modes. Each mode of the two modes may be associated with a different safe temperature range. In some embodiments, a mode of the two modes includes two stages. Each stage of the two stages may be associated with a different duration. In some embodiments, adjusting the voltage of the variable input includes reducing an amount of power provided to the heat pump (e.g., Peltier). In some embodiments, the method includes adjusting operation of a fan based on the temperature of the element.

Another implementation of the present disclosure is a lanyard to receive a thermal adjustment device. The lanyard may include a body formed of a first material having a first durometer value and a second material having a second durometer value. The lanyard may include an arm coupled to the body via a truss. In some embodiments, the truss is coupled to the body at a portion of the body formed of the second material. In some embodiments, the second durometer value is greater than the first durometer value.

In some embodiments, the first durometer value is between Shore A 30 and Shore A 45. In some embodiments, the second durometer value is between Shore A 50 and Shore A 70. In some embodiments, the body includes a pocket to receive a thermal adjustment device. In some embodiments, the body reduces impacts on the thermal adjustment device. In some embodiments, the body includes an aperture to allow a heating/cooling surface of the thermal adjustment device to contact a user. In some embodiments, a vertical axis of the body subtends an angle of 0-35 degrees relative to a vertical axis of a user. In some embodiments, the body includes a contact portion configured to contact a user. In some embodiments, the contact portion includes a coefficient of friction.

Another implementation of the present disclosure is a thermal adjustment device. In some embodiments, the thermal adjustment device includes a housing including an air intake and/or a thermal heat pump positioned within the housing and configured to receive air from the air intake. In some embodiments, the air intake includes a first aperture and a second aperture that is offset from the first aperture.

In some embodiments, the first aperture includes a slit and the second aperture includes a hole.

DETAILED DESCRIPTION

Figure 1:
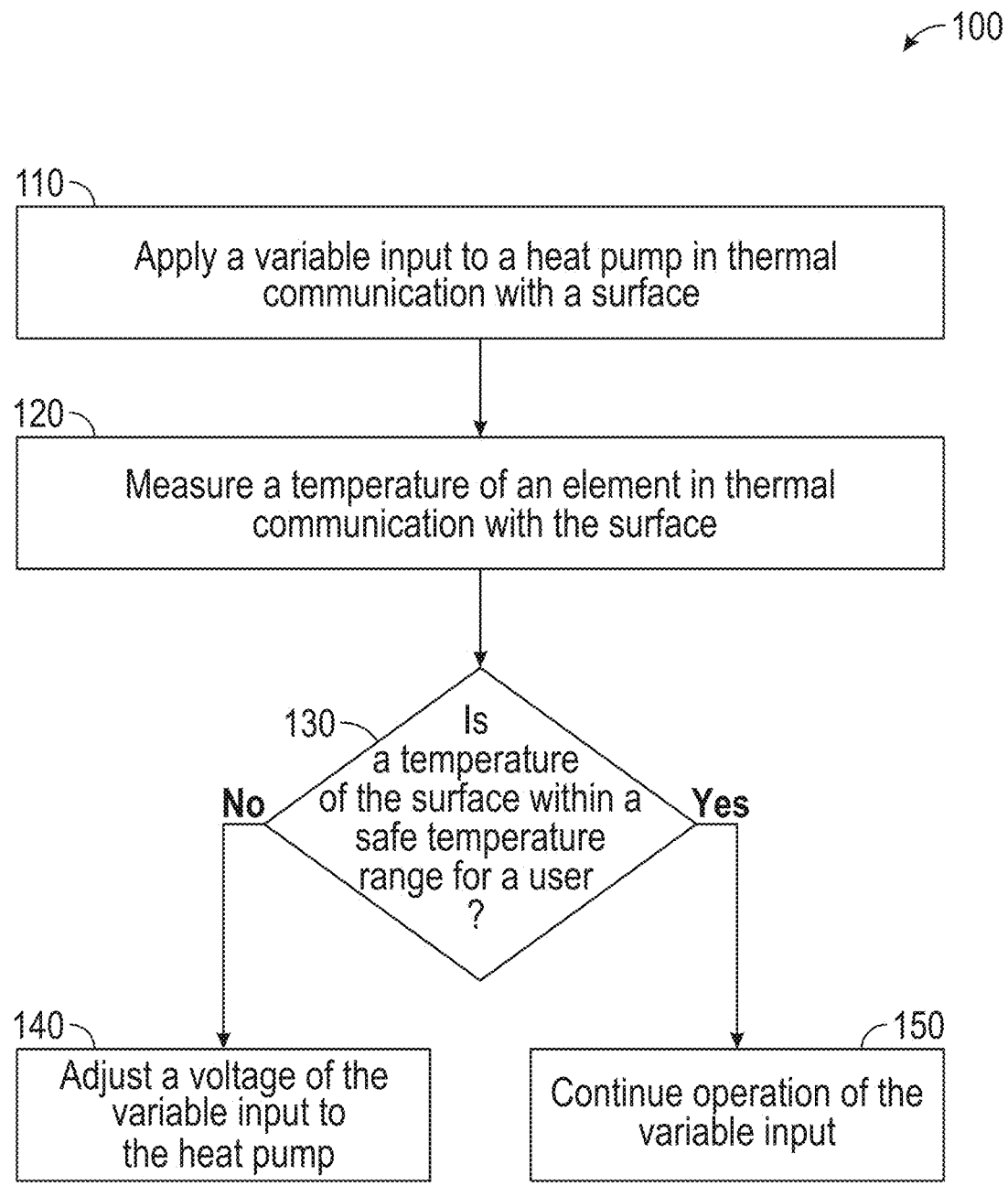
FIG. 1 illustrates an exemplary method for controlling the temperature of a surface, in accordance with an embodiment.

In the following description of embodiments, reference is made to the accompanying drawings which form a part hereof, and in which it is shown by way of illustration specific embodiments which can be practiced. It is to be understood that other embodiments can be used and structural changes can be made without departing from the scope of the disclosed embodiments.

Referring generally to the FIGURES, described herein are systems and methods for controlling the temperature of a surface. Speaking generally, disclosed herein is a thermal adjustment device and methods for operating the thermal adjustment device. In brief, the thermal adjustment device may include a thermoelectric heat pump that may be controlled to heat and/or cool a user. For example, a user may wear the thermal adjustment device in contact with their skin and the thermal adjustment device may operate to cool the user (e.g., by transferring heat from the user's skin to the environment, etc.). The user may use the thermal adjustment device to provide a comfortable personal temperature (e.g., reduce overheating, help with hot-flashes, etc.). Additionally or alternatively, the user may use the thermal adjustment device to provide localized heating/cooling. For example, in a building lacking central air-conditioning, a user may wear the thermal adjustment device to stay cool while working.

The thermal adjustment device of the present disclosure may offer many benefits over existing systems. As an example, traditional thermal adjustment devices may allow for ingress of objects to the device, thereby creating a hazardous situation. Traditional thermal adjustment devices may include a fan to facilitate heat transfer from the thermal adjustment device. However, because most thermal adjustment devices are positioned about a user's head (e.g., around a neck of the user, etc.), the fan of traditional thermal adjustment devices may interact with a user's hair. For example, a traditional thermal adjustment device may include a fan that may allow for the ingress of a user's hair, thereby causing discomfort and/or danger to the user. However, the thermal adjustment device of the present disclosure may include a baffle at an air intake of the fan to prevent ingress of objects such as hair.

Moreover, traditional thermal adjustment devices may lack active safety monitoring. For example, a traditional thermal adjustment device may rely on operating a thermoelectric heat pump within an input range to ensure user safety (e.g., safe operating temperatures, etc.). However, a temperature of the thermoelectric heat pump may vary greatly depending on a thermal load experienced by the thermoelectric heat pump. For example, a thermoelectric heat pump (e.g., in a heating scenario) may get much hotter when coupled to a small thermal load as compared to a large thermal load (e.g., holding driving power constant, etc.). To continue the example, because traditional thermal adjustment device may lack safety monitoring, they may potentially injure users (e.g., if operated without a thermal load and then applied to a user's skin, etc.). However, the thermal adjustment device of the present disclosure may solve this problem by actively monitoring a temperature associated with the thermoelectric heat pump to ensure a safe temperature range. Moreover, the thermal adjustment device may provide a comfortable personal temperature to a user. For example, the thermal adjustment device may operate a thermal heat pump using a first voltage (e.g., a maximum voltage possible for the thermal heat pump, etc.) for a first time period (e.g., to accelerate a speed of heating/cooling a thermal mass in communication with the thermal heat pump, etc.). Traditional thermal adjustment devices may not be able to achieve similar heating/cooling capacity.

Referring now to FIG. 1, method 100 for controlling the temperature of a surface is shown, according to an exemplary embodiment. In various embodiments, method 100 is performed by a thermal adjustment device. The thermal adjustment device may include a thermoelectric heat pump that may heat and/or cool a user in thermal communication with the thermoelectric heat pump. For example, a user may wear the thermal adjustment device around their neck such that the thermal adjustment device contacts the skin of the user (see, for example, FIGS. 6A-6C) and the thermal adjustment device may remove heat from the user's skin (e.g., by dissipating the heat to the environment, etc.). It should be understood that while method 100 is described in relation to a heat pump, the thermal adjustment device may include any heat pump known in the art.

At step 110, the thermal adjustment device may apply a variable input to a heat pump in thermal communication with a surface. The variable input may include a time-varying input voltage. For example, the thermal adjustment device may apply 2.8V to the heat pump for 40 seconds and then may apply 2.6V to the heat pump for 180 seconds. As another example, the thermal adjustment device may apply 2.8V to the heat pump for a first time period (e.g., 4 seconds, etc.), may measure a temperature associated with the heat pump, and in response to comparing the temperature to a threshold, may apply 2.2V to the heat pump for a second time period (e.g., 20 seconds, etc.). In some embodiments, the variable input includes a voltage range associated with a safe temperature range for a user. Additionally or alternatively, the variable input may include a safe operating voltage range for the heat pump (e.g., a voltage range that falls within an input voltage specification of the heat pump, etc.). In some embodiments, the variable input includes a number of stages. For example, the thermal adjustment device may apply a variable input having a first stage corresponding to a first input voltage and a second stage corresponding to a second input voltage, where the second input voltage changes based on a temperature feedback mechanism. To continue the example, during the second stage, the thermal adjustment device may apply a first voltage to the heat pump and may adjust the first voltage every 4 seconds in increments of 0.05V in order to achieve a setpoint temperature at a surface of the heat pump. In various embodiments, different stages correspond to different input voltages. For example, a first stage may correspond to a uniform input voltage (e.g., a steady-state 2.6V input), while a second stage may correspond to a varying input voltage (e.g., an input voltage that varies according to a sine wave (e.g., either discretely or continuously). As another example, a first stage may correspond to a steady-state input of 2.2V and a second stage may correspond to a steady-state input of 2.6V. In various embodiments, the thermal adjustment device transitions between stages based on various conditions as described in detail below with reference to FIG. 2.

In various embodiments, the thermal adjustment device controls the variable input to ensure user safety (e.g., performs safety monitoring, etc.). For example, the thermal adjustment device may control an input voltage to a heat pump based on monitoring a temperature of a surface of the heat pump in thermal communication with a user. For example, the thermal adjustment device may apply 2.8V to the heat pump for a first time period (e.g., 4 seconds, etc.), may measure a temperature associated with the heat pump, and in response to determining the temperature exceeds a threshold (e.g., a safety threshold, etc.), may apply 2.2V to the heat pump for a second time period (e.g., 20 seconds, etc.). In various embodiments, the thermal adjustment device implements one or more modes. Modes may include, for example, a heating mode and a cooling mode. Each mode may be associated with a different power level. For example, a first mode may correspond to an input voltage of 2.2V while a second mode may correspond to an input voltage of 2.6V. Each mode may include one or more stages. For example, a first mode may include three stages, where an input voltage of each stage of the three stages is within 1.7V-2.8V. To continue the example, a second mode may also include three stages, where an input voltage of each stage of the three stages is within 1.9V-3.1V.

In some embodiments, the variable input includes a powered portion (e.g., a time period corresponding to a non-zero input voltage/current) and/or an unpowered portion (e.g., a time period corresponding to a substantially zero input voltage/current). For example, during the powered portion, the thermal adjustment device may apply 2.6V (e.g., with non-zero current) to the heat pump. To continue the example, during the unpowered portion the thermal adjustment device may apply 0.0V (e.g., with zero current, with minimal leakage current, etc.) to the heat pump. Taken together, the powered portion and the unpowered portion may form a duty cycle. For example, the thermal adjustment device may apply 2.2V to the heat pump for 20 second and then 0.0V to the heat pump for 10 seconds (e.g., 66.66% duty cycle). In various embodiments, different modes and/or stages include different duty cycles. For example, a first stage of a first mode may include a 100% duty cycle (e.g., a non-zero duration powered portion and a zero duration unpowered portion, a steady-state input, etc.) and a second stage of the first mode may include a 66.66% duty cycle (e.g., a 20 second powered portion and a 10 second unpowered portion, etc.). In some embodiments, the thermal adjustment device adjusts an input voltage to the heat pump between powered/unpowered cycles. For example, the thermal adjustment device may apply 2.2V to the heat pump for 20 seconds, may then apply 0.0V to the heat pump for 10 seconds, may measure a temperature associated with the heat pump, and in response to comparing the temperature to a safety threshold, may then apply 2.25V to the heat pump for 20 seconds.

At step 120, the thermal adjustment device may measure a temperature of an element in thermal communication with the surface. For example, the thermal adjustment device may measure the temperature of a surface of the heat pump. As another example, the thermal adjustment device may measure the temperature of a thermal conductor (e.g., a heatsink, etc.) coupled to a surface of the heat pump. In various embodiments, step 120 includes measuring the temperature using a temperature sensor. The temperature sensor may include a mechanical temperature sensor and/or an electrical temperature sensor. For example, the temperature sensor may include a thermometer, a therm, a thermistor, a thermocouple, a resistance thermometer, a silicon bandgap temperature sensor, an infrared thermometer, a fiber-optic thermometer, a distributed temperature sensing (DTS) system, a pyrometer, and/or the like. In various embodiments, the element in thermal communication with the surface include a thermal conductor. For example, the element may include a metallic element (e.g., a heat pipe, etc.) coupled to the surface. As another example, the thermal adjustment device may measure a temperature of the user's skin. Additionally or alternatively, step 120 may include measuring a temperature of the surface directly.

At step 130, the thermal adjustment device may determine whether a temperature of the surface is within a safe temperature range for a user. For example, the thermal adjustment device may compare the temperature of the surface to a range to determine whether the temperature of the surface falls within the range. As another example, the thermal adjustment device may compare the temperature to a threshold. In various embodiments, the safe temperature range is between 10 degrees Centigrade (in some embodiments, 15 degrees or 10 degrees) and 49 degrees Centigrade (in some embodiments, 58 degrees or 50 degrees). For example, the thermal adjustment device may determine whether the temperature of the surface is below 49° C.

Determining whether the temperature of the surface is within the safe temperature range may include determining a temperature of the surface based on the temperature of the element in thermal communication with the surface (e.g., measured in step 120). For example, the thermal adjustment device may determine a temperature of the surface by applying a conversion factor to the temperature measured in step 120. As another example, the thermal adjustment device may determine a temperature of the surface by applying a transfer function to the temperature measured in step 120. In some embodiments, step 130 includes determining a relative temperature of the surface. For example, the thermal adjustment device may determine whether the temperature of the surface is above or below the safe temperature range (and by how much, etc.). In various embodiments, the user is in thermal communication with the surface. For example, the surface may be coupled to (e.g., in direct physical contact with, etc.) skin of the user.

If the temperature of the surface is not within a safe temperature range (No), then method 100 may proceed with step 140. At step 140, the thermal adjustment device may adjust a voltage of the variable input to the heat pump. For example, the thermal adjustment device may decrease an input voltage by 0.05V. Adjusting the voltage of the variable input may include increasing the voltage or decreasing the voltage. In various embodiments, the thermal adjustment device determines the adjustment based on the temperature of the surface. For example, if the temperature is above a threshold (e.g., a setpoint, etc.), the thermal adjustment device may decrease the voltage applied to the heat pump by 0.05V. As another example, if the temperature is below a threshold, the thermal adjustment device may increase the voltage applied to the heat pump by 0.05V.

In some embodiments, the thermal adjustment device determines a step size of the adjustment based on a magnitude of the difference between the temperature of the surface and a target (e.g., a setpoint, a threshold, a temperature range, etc.). For example, the thermal adjustment device may increase an input voltage by 1.0V in response to determining a 5° C. difference between the temperature of the surface and a setpoint and may increase the input voltage by 0.5V in response to determining a 3° C. difference between the temperature of the surface and a setpoint. In some embodiments, the thermal adjustment device implements a proportional-integral derivative control scheme. For example, the thermal adjustment device may apply a large voltage adjustment when a temperature of the surface is far from a setpoint and may apply a small voltage adjustment when the temperature of the surface is close to the setpoint. In some embodiments, step 140 includes depowering the heat pump. For example, the thermal adjustment device may apply 0.0V to the heat pump. If the temperature of the surface is within a safe temperature range (Yes), then method 100 may proceed with step 150. At step 150, the thermal adjustment device may continue operation of the variable input. For example, the thermal adjustment device may continue providing the same input voltage to the heat pump.

Figure 2:
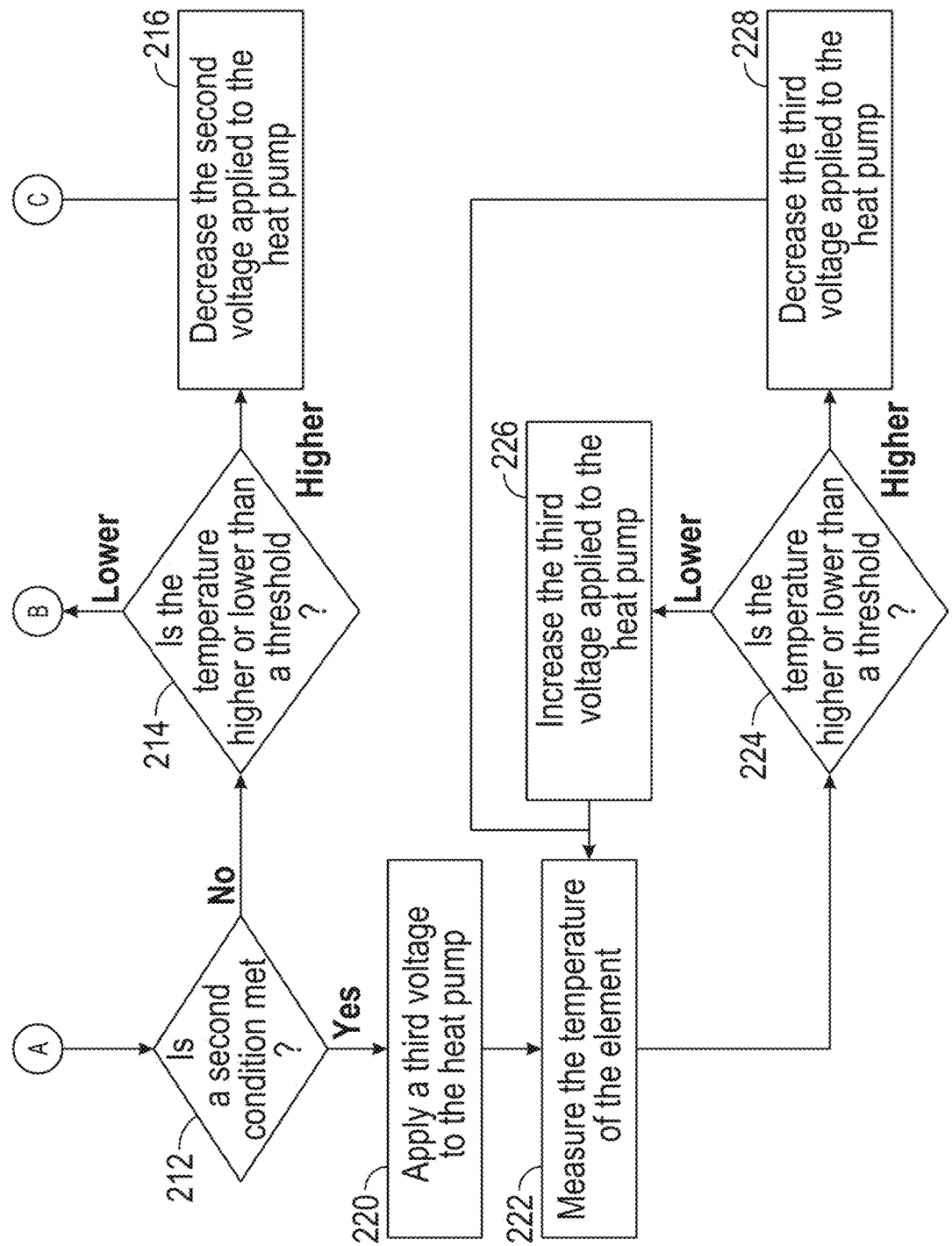
FIG. 2 illustrates another exemplary method for controlling the temperature of a surface, in accordance with an embodiment.

Referring now to FIG. 2, method 200 for determining an input for a thermoelectric heat pump is shown, according to an exemplary embodiment. In various embodiments, the thermal adjustment device performs method 200. For example, the thermal adjustment device may implement method 200 to heat and/or cool a user. In various embodiments, the thermoelectric heat pump includes a heat pump. In brief, the thermal adjustment device may operate the heat pump in a number of stages. Each stage may correspond to a different duration and/or input characteristics. Steps 202-206 may correspond to a first stage, steps 208-218 may correspond to a second stage, and/or steps 220-228 may correspond to a third stage. In various embodiments, the thermal adjustment device implements one or more cooling modes. In some embodiments, the thermal adjustment device implements a first stage of a number of cooling modes as described in the table below.

| | First stage (e.g., 40 sec) | | |
|---|---|---|---|
| | First portion (e.g., 20 sec) | Second portion (e.g., 20 sec) | |
| | Input to heat pump | Input to heat pump | Function |
| First cooling mode | 2.8 V | 2.8 V | Monitor temperature periodically (e.g., every 10 sec) If temperature < threshold (e.g., 23° C.), start second stage with 2.2 V If temperature within range (e.g., 23° C. to 25° C.), start second stage with 2.4 V If ((time ≥ 40 sec) AND (temperature < threshold) (e.g., 24.5° C.)), start second stage with 2.6 V If ((time ≥ 40 sec) AND (temperature ≥ threshold) (e.g., 24.5° C.)), start second stage with 2.8 V |
| Second cooling mode | 3.4 V | 3.4 V | Monitor temperature periodically (e.g., every 10 sec) If temperature < threshold (e.g., 21° C.), start second stage with 2.2 V If temperature within range (e.g., 21° C. to 23° C.), start second stage with 2.5 V If ((time ≥ 40 sec) AND (temperature < threshold) (e.g., 22.5° C.)), start second stage with 2.8 V If ((time > 40 sec) AND (temperature > threshold) (e.g., 22.5° C.)), start second stage with 3.4 V |
| Third cooling mode | 4.0 V | 4.0 V | Monitor temperature periodically (e.g., every 10 sec) If temperature < 20° C., start second stage with 2.2 V If temperature within range (e.g., 20° C. to 22° C.), start second stage with 2.8 V If ((time ≥ 40 sec) AND (temperature < threshold) (e.g., 21.5° C.)), start second stage with 3.4 V If ((time ≥ 40 sec) AND (temperature ≥ threshold) (e.g., 21.5° C.)), start second stage with 4.0 V |

It should be understood that while the tables of the present disclosure include exemplary monitoring periods (e.g., 4 seconds, 10 seconds, etc.), any monitoring period may be used. For example, the thermal adjustment device may monitor a temperature of a surface in continuously (e.g., every 10 milliseconds, etc.). In some embodiments, the first portion (e.g., 20 seconds, etc.) facilitates providing a timely comfortable temperature to a user (e.g., quickly cooling the user, etc.). In some embodiments, the second portion (e.g., 20 seconds, etc.) facilitates providing a comfortable temperature to a user within a time period (e.g., to avoid cooling a temperature of the heat pump too quickly, etc.). It should be understood that while the tables of the present disclosure include exemplary temperature values (e.g., thresholds, ranges, setpoints, etc.), any temperature value may be used that facilitates performance of the thermal adjustment device (e.g., is within a safe temperature range for a user, etc.). In some embodiments, the thermal adjustment device implements a second stage of the number of cooling modes as described in the table below.

| | Second stage (e.g., 180 sec) Stabilization | |
|---|---|---|
| | Input to heat pump | Function |
| First cooling mode | 1.7 V~2.8 V | Monitor temperature periodically (e.g., every 4 sec) Target setpoint (e.g., 23° C.) Start duty cycle at 50% If temperature < threshold (e.g., 23° C.), decrease PWM 10%. If PWM at 10%, decrease voltage by step size (e.g., 0.15 V) If temperature ≥ threshold (e.g., 23° C.), increase PWM 10%. If PWM at 90%, increase voltage by step size (e.g., 0.15 V) |
| Second cooling mode | 1.7 V~3.4 V | Monitor temperature periodically (e.g., every 4 sec) Target setpoint (e.g., 21° C.) Start duty cycle at 50% If temperature < threshold (e.g., 21° C.), decrease PWM 10%. If PWM at 10%, decrease voltage by step size (e.g., 0.15 V) If temperature ≥ threshold (e.g., 21° C.), increase PWM 10%. If PWM at 90%, increase voltage by step size (e.g., 0.15 V) |

-continued

| | Second stage (e.g., 180 sec) Stabilization | |
|---|---|---|
| | Input to heat pump | Function |
| Third cooling mode | 1.7 V~4.0 V | Monitor temperature periodically (e.g., every 4 sec) Target setpoint (e.g., 20° C.) Start duty cycle at 50% If temperature < threshold (e.g., 20° C.), decrease PWM 10%. If PWM at 10%, decrease voltage by step size (e.g., 0.15 V) If temperature ≥ threshold (e.g., 20° C.), increase PWM 10%. If PWM at 90%, increase voltage by step size (e.g., 0.15 V) |

Additionally or alternatively, the thermal adjustment device may implement the second stage of the number of cooling modes as described in the table below.

| | Second stage (e.g., 180 sec) Stabilization | |
|---|---|---|
| | Input to heat pump | Function |
| First cooling mode | 1.7 V~2.8 V | Monitor temperature periodically (e.g., every 4 sec) Target setpoint (e.g., 23° C.) If temperature > setpoint (e.g., 23° C.), increase input by step size (e.g., 0.05 V) If temperature < setpoint (e.g., 23° C.), decrease input by step size (e.g., 0.05 V) |
| Second cooling mode | 1.7 V~3.4 V | Monitor temperature periodically (e.g., every 4 sec) Target setpoint (e.g., 21° C.) If temperature > setpoint (e.g., 21° C.), increase input by step size (e.g., 0.1 V) If temperature < setpoint (e.g., 21° C.), decrease input by step size (e.g., 0.1 V) |
| Third cooling mode | 1.7 V~4.0 V | Monitor temperature periodically (e.g., every 4 sec) Target setpoint (e.g., 20° C.) If temperature > setpoint (e.g., 20° C.), increase input by step size (e.g., 0.15 V) If temperature < setpoint (e.g., 20° C.), decrease input by step size (e.g., 0.15 V) |

In some embodiments, the thermal adjustment device 40 implements a third stage of the number of cooling modes as described in the table below.

| | Third stage Waved: Powered period (e.g., 20 sec)/unpowered period (e.g., 10 sec) | |
|---|---|---|
| | Input to heat pump | Function |
| First cooling mode | 1.7 V~2.8 V | Monitor temperature periodically (e.g., every 30 sec) Target setpoint (e.g., 23° C.) Start with same input as end of Second Stage If temperature < threshold (e.g., 23° C.), decrease PWM 10%. If PWM at 10%, decrease voltage by step size (e.g., 0.15 V) If temperature > threshold (e.g., 23° C.), increase PWM 10%. If PWM at 90%, increase voltage by step size (e.g., 0.15 V) |
| Second cooling mode | 1.7 V~3.4 V | Monitor temperature periodically (e.g., every 30 sec) Target setpoint (e.g., 21° C.) Start with same input as end of Second Stage If temperature < threshold (e.g., 21° C.), decrease PWM 10%. If PWM at 10%, decrease voltage by step size (e.g., 0.15 V) If temperature > threshold (e.g., 21° C.), increase PWM 10%. If PWM at 90%, increase voltage by step size (e.g., 0.15 V) |
| Third cooling mode | 1.7 V~4.0 V | Monitor temperature periodically (e.g., every 30 sec) Target setpoint (e.g., 20° C.) Start with same input as end of Second Stage If temperature < threshold (e.g., 20° C.), decrease PWM 10%. If PWM at 10%, decrease voltage by step size (e.g., 0.15 V) If temperature > threshold (e.g., 20° C.), increase PWM 10%. If PWM at 90%, increase voltage by step size (e.g., 0.15 V) |

Additionally or alternatively, the thermal adjustment device may implement the third stage of the number of cooling modes as described in the table below.

| | Third stage Waved: Powered period (e.g., 20 sec)/unpowered period (e.g., 10 sec) | |
|---|---|---|
| | Input to heat pump | Function |
| First cooling mode | 1.7 V~2.8 V | Monitor temperature periodically (e.g., every 30 sec) Target setpoint (e.g., 23° C.) Start with same input as end of Second Stage If temperature < threshold (e.g., 23° C.), decrease voltage by step size (e.g., 0.05 V) If temperature ≥ threshold (e.g., 23° C.), increase voltage by step size (e.g., 0.05 V) |
| Second cooling mode | 1.7 V~3.4 V | Monitor temperature periodically (e.g., every 30 sec) Target setpoint (e.g., 21° C.) Start with same input as end of Second Stage If temperature < threshold (e.g., 21° C.), decrease voltage by step size (e.g., 0.1 V) If temperature ≥ threshold (e.g., 21° C.), increase voltage by step size (e.g., 0.1 V) |
| Third cooling mode | 1.7 V~4.0 V | Monitor temperature periodically (e.g., every 30 sec) Target setpoint (e.g., 20° C.) Start with same input as end of Second Stage If temperature < threshold (e.g., 20° C.), decrease voltage by step size (e.g., 0.15 V) If temperature ≥ threshold (e.g., 20° C.), increase voltage by step size (e.g., 0.15 V) |

It should be understood that while the tables of the present disclosure include exemplary time periods (e.g., a duration of a powered/unpowered period, etc.), any time period may be used that facilitates performance of the thermal adjustment device. Additionally or alternatively, the thermal adjustment device may implement a number of heating modes. In some embodiments, the thermal adjustment device implements a first stage of a number of heating modes as described in the table below.

| | First stage First portion (e.g., 40 sec) | |
|---|---|---|
| | Input to heat pump | Function |
| First heating mode | 2.2 V | Monitor temperature periodically (e.g., every 1 sec, every 4 sec) If temperature > threshold (e.g., 38° C.), start second stage with 1.75 V If time > 40 sec, start second stage with 1.75 V |
| Second heating mode | 2.8 V | Monitor temperature periodically (e.g., every 1 sec, every 4 sec) If temperature > threshold (e.g., 39° C.), start second stage with 1.8 V If time > 40 sec, start second stage with 1.8 V |
| Third heating mode | 3.4 V | Monitor temperature periodically (e.g., every 1 sec, every 4 sec) If temperature > threshold (e.g., 40° C.), start second stage with 1.9 V If time > 40 sec, start second stage with 1.9 V |

In some embodiments, the thermal adjustment device implements a second stage of a number of heating modes as described in the table below.

| | Second stage Stabilization | |
|---|---|---|
| | Input to heat pump | Function |
| First heating mode | 1.7 V~2.2 V | Monitor temperature periodically (e.g., every 1 sec, every 4 sec) If temperature > threshold (e.g., 46° C.), power off until temperature ≤ threshold (e.g., 39.5° C.) If temperature < threshold (e.g., 39.5° C.), increase voltage by step size (e.g., 0.05 V) |
| Second heating mode | 1.7 V~2.8 V | Monitor temperature periodically (e.g., every 1 sec, every 4 sec) If temperature > threshold (e.g., 46° C.), power off until temperature ≤ threshold (e.g., 40.5° C.) If temperature < threshold (e.g., 40.5° C.), increase voltage by step size (e.g., 0.1 V) |

|  | Second stage Stabilization | |
|---|---|---|
|  | Input to heat pump | Function |
| Third heating mode | 1.7 V~3.4 V | Monitor temperature periodically (e.g., every 1 sec, every 4 sec)<br>If temperature > threshold (e.g., 46° C.), power off until temperature ≤ threshold (e.g., 41.5° C.)<br>If temperature < threshold (e.g., 41.5° C.), increase voltage by step size (e.g., 0.15 V) |

Additionally or alternatively, the thermal adjustment device may implement the second stage of the number of heating modes as described in the table below.

|  | Second stage Stabilization | |
|---|---|---|
|  | Input to heat pump | Function |
| First heating mode | 1.7 V~2.2 V | Monitor temperature periodically (e.g., every 1 sec, every 4 sec)<br>Duty cycle starts at 10% (e.g., 1.7 V at 90% & 2.2 V at 10%)<br>If temperature < threshold (e.g., 39.5° C.), increase duty cycle 10% (e.g., to a maximum of 90%)<br>If temperature > threshold (e.g., 46° C.), power off until temperature 0.2° C. |
| Second heating mode | 1.7 V~2.8 V | Monitor temperature periodically (e.g., every 1 sec, every 4 sec)<br>Duty cycle starts at 10% (e.g., 1.7 V at 90% & 2.2 V at 10%)<br>If temperature < threshold (e.g., 40.5° C.), increase duty cycle 10% (e.g., to a maximum of 90%)<br>If temperature > threshold (e.g., 46° C.), power off until temperature 0.2° C. |
| Third heating mode | 1.7 V~3.4 V | Monitor temperature periodically (e.g., every 1 sec, every 4 sec)<br>Duty cycle starts at 10% (e.g., 1.7 V at 90% & 2.2 V at 10%)<br>If temperature < threshold (e.g., 41.5° C.), increase duty cycle 10% (e.g., to a maximum of 90%)<br>If temperature > threshold (e.g., 46° C.), power off until temperature 0.2° C. |

As mentioned above, the thermal adjustment device implements a number of modes. Each mode may correspond to a different heating/cooling intensity (e.g., low, medium, high, etc.). For example, a first mode may deliver a first amount of cooling (e.g., heat transfer) to a user and a second mode may deliver a second amount of cooling to a user that is greater than the first amount of cooling. In various embodiments, the thermal adjustment device achieves different levels of heating/cooling by applying different input voltages to the heat pump, thereby changing a temperature of a surface in thermal communication with the user. For example, the thermal adjustment device may cool a user a small amount by applying 1.0V to the heat pump and may cool the user a larger amount by applying 2.0V to the heat pump. Method 200 may correspond to a single mode. For example, method 200 may correspond to a first mode having a first input voltage range to achieve a first amount of heat transfer. In various embodiments, a user selects different heating/cooling modes using a user interface as described below.

To implement different modes (e.g., different amounts of heat transfer, different intensities of heating/cooling, etc.), the thermal adjustment device may implement method 200 using different voltage values. For example, in a first cooling mode the thermal adjustment device may implement method 200 using a first voltage range and in a second cooling mode the thermal adjustment device may implement method 200 using a second voltage range (e.g., where voltages of the first voltage range are less than voltages of the second voltage range, etc.). Therefore, it should be understood that while method 200 is described in relation to various input voltages, other voltages may be used (e.g., corresponding to different modes, etc.).

At step 202, the thermal adjustment device may apply a first voltage to a heat pump. For example, the thermal adjustment device may apply 2.8V to a heat pump (e.g., create an electrical potential of 2.8V between inputs of the heat pump, etc.). In some embodiments, the thermal adjustment device applies the first voltage to the heat pump for a time period. For example, in a first cooling mode (e.g., low cooling) the thermal adjustment device may apply 2.8V to the heat pump for a period of 20 seconds. As another example, in a second cooling mode (e.g., medium cooling) the thermal adjustment device may apply 3.4V to the heat pump for 20 seconds. As yet another example, in a third cooling mode (e.g., high cooling) the thermal adjustment device may apply 4.0V to the heat pump for 20 seconds.

At step 204, the thermal adjustment device may measure a temperature of an element in thermal communication with the heat pump. For example, the thermal adjustment device may measure the temperature of a surface of the heat pump. As another example, the thermal adjustment device may measure the temperature of a thermal conductor coupled to a surface of the heat pump and determine a temperature of a surface of the heat pump based on the temperature of the thermal conductor as described above with reference to FIG. 1.

At step 206, the thermal adjustment device may determine whether a first condition is met. Determining whether the first condition is met may include determining whether the temperature of the element is within a temperature range. For example, the thermal adjustment device may compare a temperature of a surface of the heat pump (e.g., determined in step 204) to a threshold. Additionally or alternatively, determining whether the first condition is met may include determining whether the first input has been applied for a threshold time period. For example, the thermal adjustment device may determine that the first condition is met if the thermal adjustment device has operated in the first stage (e.g., steps 202-206) for 40 seconds and a temperature of a surface of the heat pump is greater than a threshold. In some embodiments, the thermal adjustment device operates in the first stage for a time period (e.g., to allow the thermal adjustment device to build up a thermal mass, to timely provide a comfortable personal temperature to a user, etc.). In some embodiments, the time period is adjusted to change a battery life of the thermal adjustment device (e.g., the time period is shortened to increase a battery life of the thermal adjustment device, etc.).

In various embodiments, the first condition includes a number of sub-conditions. For example, the first condition may be implemented as:

IF ((temperature<23° C.) OR (temperature<24.5° C. AND time≥40 seconds) OR (temperature>24.5° C. AND time≥40 seconds)) THEN(perform step 208)

In some embodiments, steps 204-206 are performed periodically. For example, the thermal adjustment device may perform steps 204-206 every 4 seconds. To continue the example, the thermal adjustment device may apply the first voltage to the heat pump for 20 seconds and after the 20 seconds may monitor a temperature of the heat pump every 4 seconds to determine whether the first condition is satisfied (e.g., steps 204-206).

If the first condition is not satisfied (No), method 200 may proceed with step 202 (e.g., continue applying the first voltage to the heat pump). In various embodiments, the thermal adjustment device repeats steps 202-206 until the first condition (or one of the number of sub-conditions) is satisfied. If the first condition is satisfied (Yes), method 200 may proceed with step 208. At step 208, the thermal adjustment device may apply a second voltage to the heat pump. For example, the thermal adjustment device may apply 2.6V to the heat pump. In some embodiments, the thermal adjustment device applies the second voltage to the heat pump for a time period. For example, in a first cooling mode (e.g., low cooling) the thermal adjustment device may apply the second voltage to the heat pump for a period of 180 seconds.

In various embodiments, the second voltage is determined based on a result of step 206. For example, if the temperature of the surface of the heat pump is less than 23° C. at step 206, then the thermal adjustment device may apply 2.2V to the heat pump. In some embodiments, the second voltage is the same as the first voltage. In various embodiments, the thermal adjustment device determines the second voltage according to the relationships:

IF (temperature<23° C.)→second voltage=2.2V IF (temperature<24.5° C. AND time 40 seconds)→second voltage=2.6V IF (temperature>24.5° C. AND time 40 seconds)→second voltage=2.8V At step 210, the thermal adjustment device may measure a temperature of the element. For example, the thermal adjustment device may measure the temperature of a surface of the heat pump. Additionally or alternatively, the thermal adjustment device may measure the temperature of the element using any other means described with respect to step 120 above. At step 212, the thermal adjustment device may determine whether a second condition is met. For example, the thermal adjustment device may determine whether the second voltage has been applied for a threshold amount of time (e.g., 180 seconds, etc.). In various embodiments, the second condition is implemented as:

IF (time≥180 seconds) T HEN (perform step 220)

If the first condition is not satisfied (No), method 200 may proceed with step 214. If the first condition is satisfied (Yes), method 200 may proceed with step 220. At step 214, the thermal adjustment device may determine whether the temperature of the element is higher or lower than a threshold. In various embodiments, the threshold is a setpoint. For example, in a first cooling mode the threshold may be a setpoint of 23° C. As another example, in a second cooling mode the threshold may be a setpoint of 21° C. As yet another example, in a third cooling mode the threshold may be a setpoint of 20° C.

If the temperature of the element is higher than the threshold, method 200 may proceed with step 216. If the temperature of the element is lower than the threshold, method 200 may proceed with step 218. In various embodiments, if the temperature of the element is equal to the threshold, then method 200 proceeds with step 210 (e.g., at the next sampling interval, etc.). At step 216, the thermal adjustment device may decrease the second voltage applied to the heat pump. For example, the thermal adjustment device may decrease the second voltage by 0.05V. At step 218, the thermal adjustment device may increase the second voltage applied to the heat pump. For example, the thermal adjustment device may increase the second voltage by 0.05V. In various embodiments, the thermal adjustment device repeats steps 210-218 until the second condition is met.

At step 220, the thermal adjustment device may apply a third voltage to the heat pump. For example, the thermal adjustment device may apply the same voltage applied in step 208. To continue the example, the thermal adjustment device may apply a voltage of 2.6V in step 208, may increase the voltage in steps 0.05V to 2.75V in steps 210-218, and may apply 2.75V in step 220.

At step 222, the thermal adjustment device may measure the temperature of the element. For example, the thermal adjustment device may measure the temperature of a surface of the heat pump. Additionally or alternatively, the thermal adjustment device may measure the temperature of the element using any other means described with respect to step 120 above. At step 224, the thermal adjustment device may determine whether the temperature of the element is higher or lower than a threshold. For example, the thermal adjustment device may compare the temperature to a threshold. In various embodiments, the threshold is a setpoint. For example, in a first cooling mode the threshold may be a setpoint of 23° C. As another example, in a second cooling mode the threshold may be a setpoint of 21° C. As yet another example, in a third cooling mode the threshold may be a setpoint of 20° C. In some embodiments, the threshold of step 224 is different than the threshold of step 214. Additionally or alternatively, the threshold of step 224 may be the same as the threshold of step 214.

If the temperature of the element is higher than the threshold, method 200 may proceed with step 226. If the temperature of the element is lower than the threshold, method 200 may proceed with step 228. In various embodiments, if the temperature of the element is equal to the threshold, then method 200 proceeds with step 222 (e.g., at the next sampling interval, etc.). At step 226, the thermal adjustment device may increase the voltage applied to the heat pump. For example, the thermal adjustment device may increase the third voltage by 0.05V. At step 228, the thermal adjustment device may decrease the voltage applied to the heat pump. For example, the thermal adjustment device may decrease the third voltage by 0.05V. In various embodiments, steps 222-228 are performed periodically. For example, the thermal adjustment device may monitor a temperature of the element and update the third voltage every 30 seconds. However, it should be understood that other periods are possible (e.g., every second, every hour, etc.). Moreover, it should be understood that other voltage adjustments amounts (e.g., 1.0V, 1.1V, 4.0V, etc.) are possible.

Figure 3A:
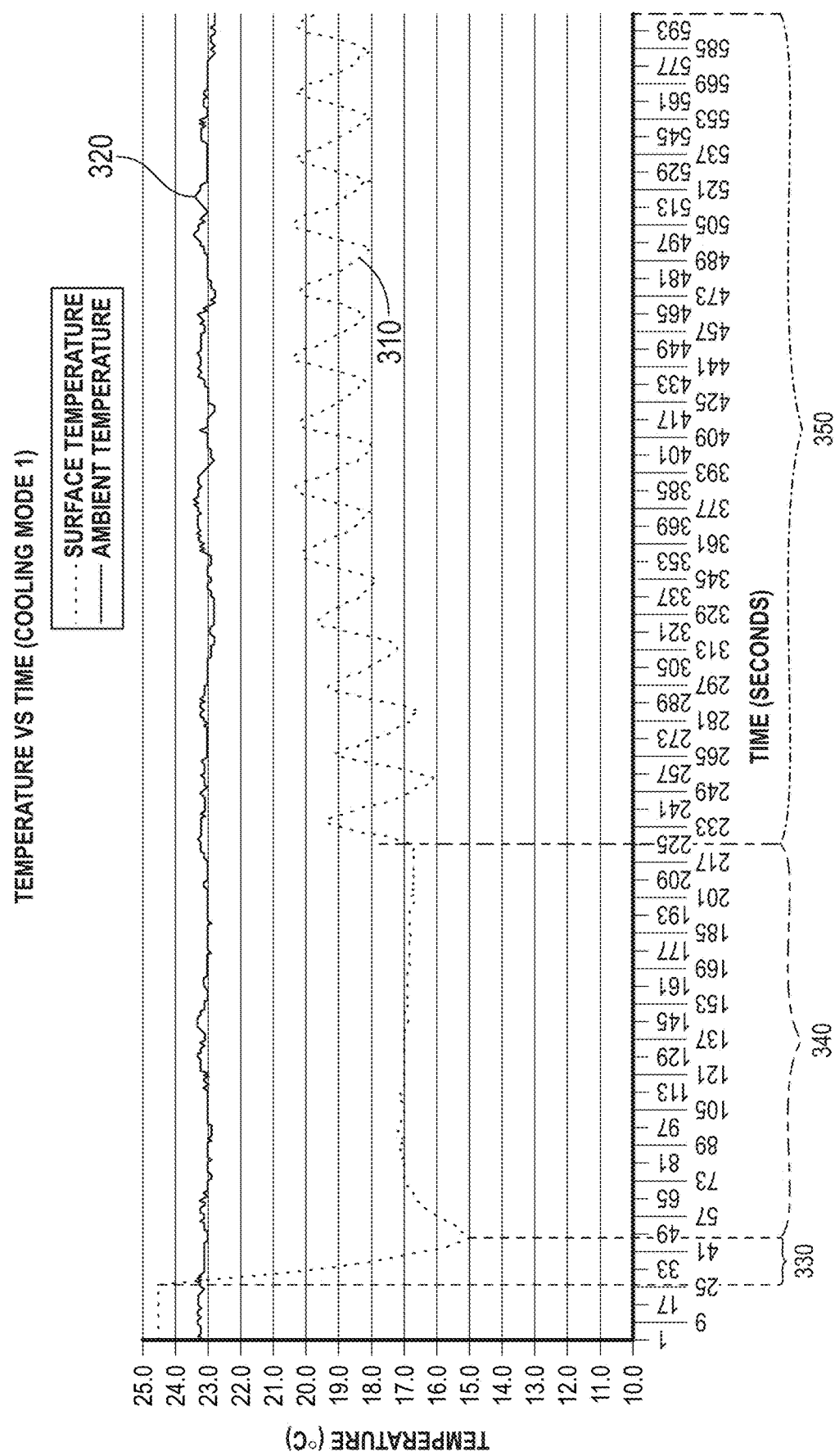
FIGS. 3A-L are graphs illustrating exemplary temperature profiles of a thermal adjustment device in operation, in accordance with an embodiment.
Figure 3B:
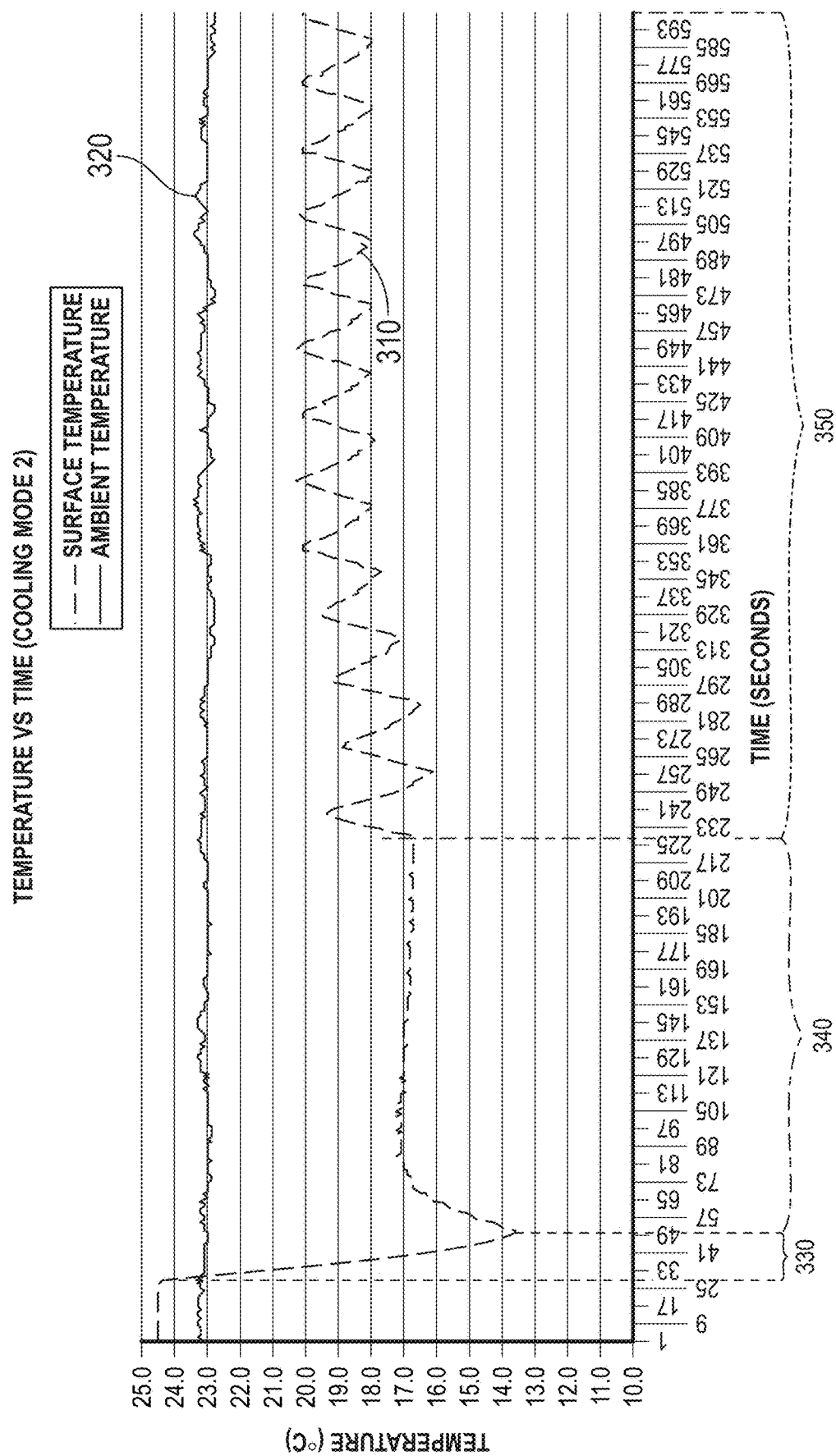
Figure 3C:
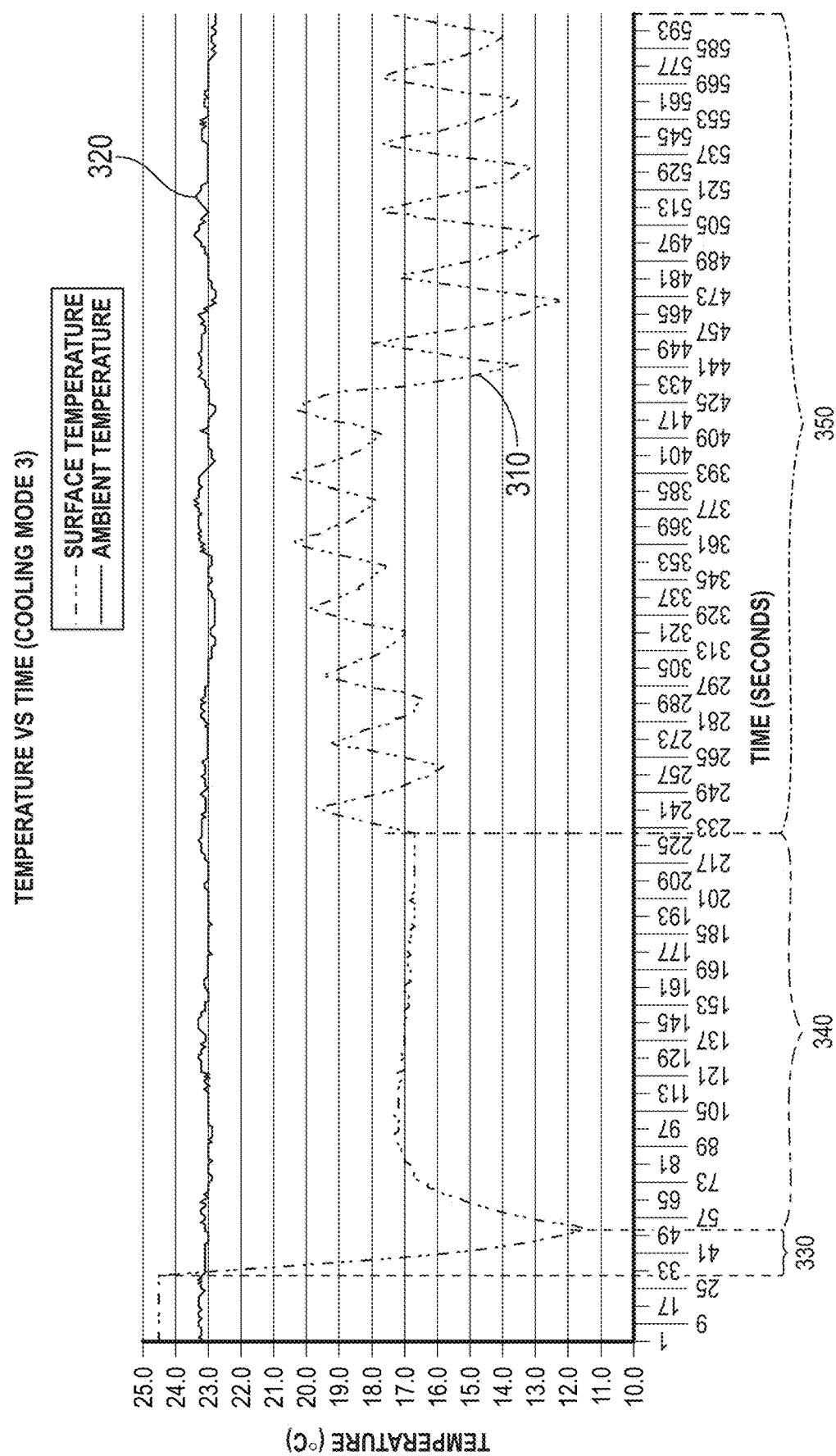
Figure 3D:
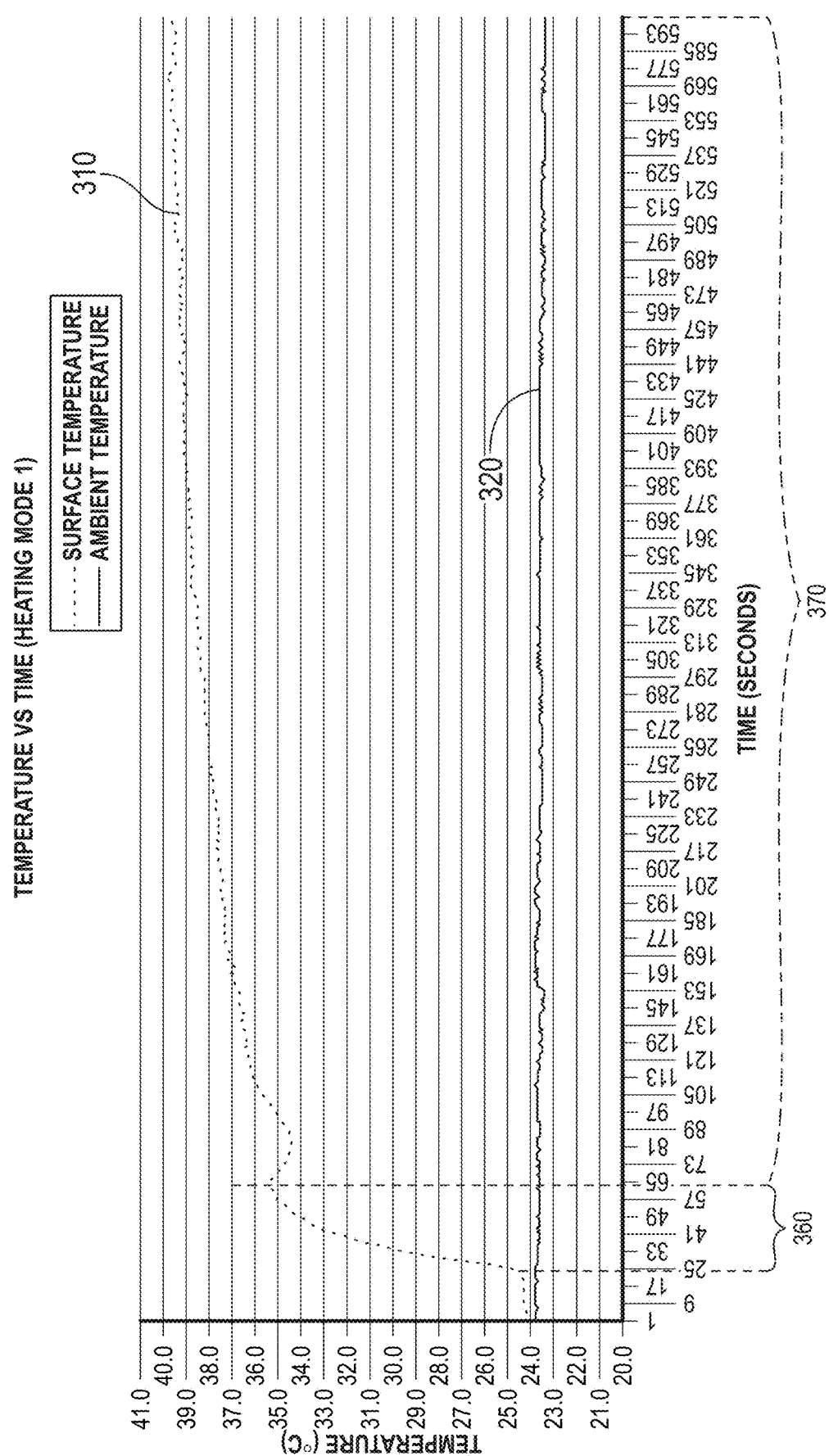
Figure 3E:
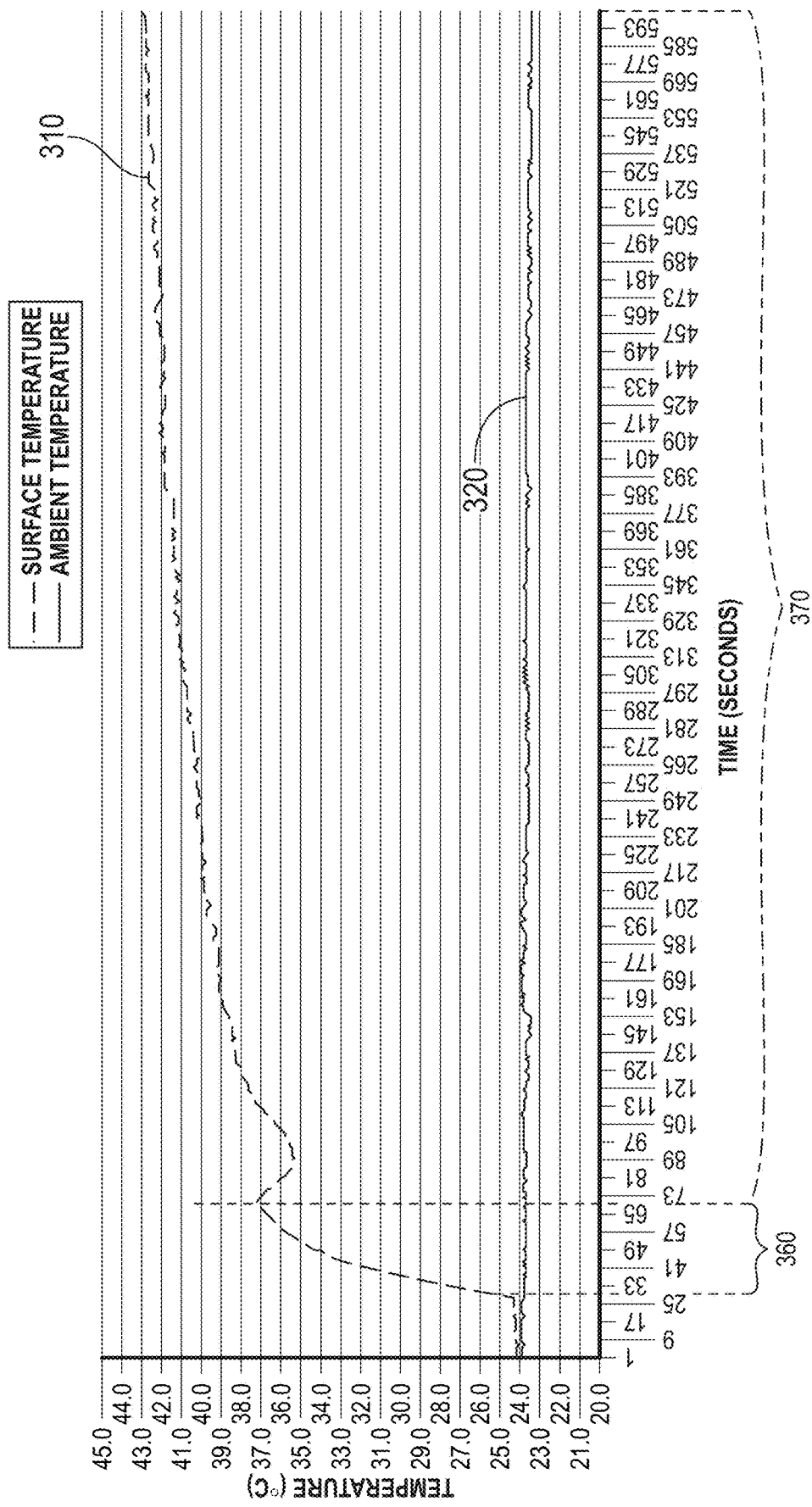
Figure 3F:
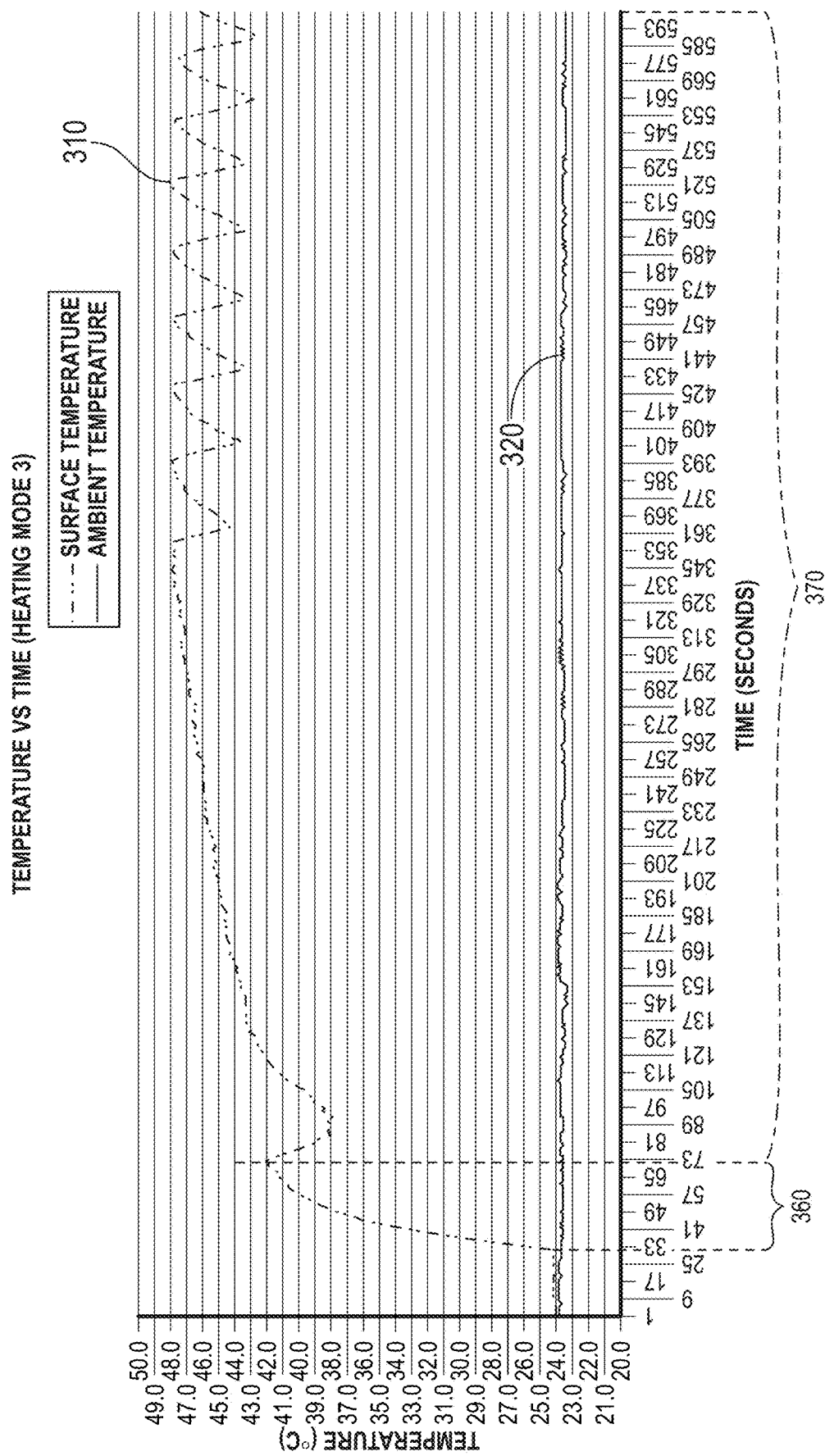

Referring now to FIGS. 3A-L, a number of graphs illustrating temperature profiles of a thermal adjustment device are shown, according to an exemplary embodiment. In various embodiments, the graphs illustrate a temperature of a contact surface of the thermal adjustment device during different stages of an operating mode. FIG. 3A illustrates temperature measurements of a surface in thermal communication with a user during three stages of a first cooling mode. In some embodiments, the surface is directly contacting the user's skin; in other embodiments, intermediate structure separates the surface and the user's skin. FIG. 3B illustrates temperature measurements of a surface in thermal communication with a user during three stages of a second cooling mode. FIG. 3C illustrates temperature measurements of a surface in thermal communication with a user during three stages of a third cooling mode. FIG. 3D illustrates temperature measurements of a surface in thermal communication with a user during two stages of a first heating mode. FIG. 3E illustrates temperature measurements of a surface in thermal communication with a user during two stages of a second heating mode. FIG. 3F illustrates temperature measurements of a surface in thermal communication with a user during two stages of a third heating mode. As shown, the graphs include surface temperature 310 and ambient temperature 320. Surface temperature 310 may correspond to a temperature of a surface of the thermal adjustment device. For example, surface temperature 310 may be a temperature of a surface of the thermal adjustment device that is in thermal communication with a user (e.g., in contact with a user's skin, etc.). Ambient temperature 320 may correspond to a temperature of the ambient environment. For example, ambient temperature 320 may correspond to a temperature of a room the thermal adjustment device is operating within.

In various embodiments, the thermal adjustment device operates in various stages. For example, in a first cooling mode (e.g., shown in FIG. 3A), the thermal adjustment device may operate in three stages: (i) an initialization stage, (ii) a stabilization stage, and (iii) a waved cool stage. As another example, in a first heating mode (e.g., shown in FIG. 3D), the thermal adjustment device may operate in two stages: (i) an initialization stage and (ii) a stabilization stage. FIGS. 3A-3C are shown to include first stage 330, second stage 340, and third stage 350. First stage 330 may correspond to steps 202-206 of FIG. 2. Second stage 340 may correspond to steps 208-218 of FIG. 2. Third stage 350 may correspond to steps 220-228 of FIG. 2. FIGS. 3D-3F are shown to include first stage 360 and second stage 370.

In brief, in first stage 330 the thermal adjustment device may apply a first voltage to the heat pump for a time period (e.g., 20 second, 40 seconds, etc.) and/or until a temperature threshold is met. For example, the thermal adjustment device applies 2.8 Volts to the heat pump for 20 seconds. In some embodiments, the time period is static (e.g., 20 seconds). Additionally or alternatively, the time period is dynamic (e.g., changes based on conditions). For example, the thermal adjustment device applies 2.8 Volts to the heat pump until a temperature of a surface of the heat pump is determined to exceed a threshold. In some embodiments, the first voltage corresponds to a maximum cooling intensity. Advantageously, in first stage 330 the thermal adjustment device may operate the heat pump at a maximum cooling intensity to timely provide a comfortable personal temperature to a user (e.g., cool the user quickly). In second stage 340, the thermal adjustment device may apply a second voltage to the heat pump for a time period (e.g., 180 seconds, etc.) and may adjust the second voltage to achieve a temperature setpoint (e.g., threshold, etc.). In third stage 350, the thermal adjustment device may apply a third voltage to the heat pump during a powered period (e.g., 20 seconds, etc.), may remove power from the heat pump during an unpowered period (e.g., 10 second, etc.), and may adjust the third voltage to achieve a temperature setpoint (e.g., a threshold, etc.). In various embodiments, third stage 350 corresponds to a waved cooling mode (e.g., an oscillation between two temperatures, etc.). Advantageously, by varying a temperature of the surface, the waved cooling mode may provide a comfortable personal temperature for a user (e.g., as opposed to cooling to a static temperature, etc.). In various embodiments, a waved cooling mode reduces a user's habituation to a cooling sensation (e.g., as opposed to cooling to a static temperature, etc.), thereby improving a user's subjective sense of cooling relief. In various embodiments, the temperature setpoints are associated with a mode. For example, in a first cooling mode (e.g., low) the temperature setpoint may be 23° C. In a second cooling mode (e.g., medium) the temperature setpoint may be 21° C. In a third cooling mode (e.g., high) the temperature setpoint may be 20° C.

Referring still to FIGS. 3A-3C, in first stage 330, the thermal adjustment device may apply a first voltage to the heat pump (thereby causing a surface in thermal communication with a user to cool) for a time period (e.g., 20 seconds). At the end of the time period, the thermal adjustment device may determine that the temperature of the surface is lower than a threshold (e.g., 23° C.) and may transition to second stage 340. In second stage 340, the thermal adjustment device may apply a second voltage (e.g., 2.2V, etc.) to the heat pump for a time period (e.g., 180 second, etc.). In various embodiments, the second voltage is determined based on a temperature of the surface in first stage 330. For example, in a first cooling mode the thermal adjustment device may implement the function:

IF (temperature<23° C.)→terminate first stage and begin second stage with 2.2V

IF (temperature<24.5° C. AND time≥40 seconds)→terminate first stage and begin second stage with 2.6V IF (temperature 24.5° C. and time≥40 seconds)→terminate first stage and begin second stage with 2.8V At the end of the time period, the thermal adjustment device may transition to third stage 350. In third stage 350, the thermal adjustment device may apply a variable input including a powered period and an unpowered period. For example, the thermal adjustment device may apply an input having a 66% duty cycle. In some embodiments, the powered period is 20 seconds and the unpowered period is 10 seconds. However, it should be understood that other durations for the powered period and/or the unpowered period are possible. In some embodiments, the thermal adjustment device implements the function:

IF (temperature<threshold (e.g., 23° C.))→decrease a voltage of the variable input by step size (e.g., 0.05V)

IF (temperature>threshold (e.g., 23° C.))→increase a voltage of the variable input by step size (e.g., 0.05V)

It should be understood that other temperature thresholds and/or voltage adjustments (e.g., steps of 1V, 2V, etc.) are possible. For example, in a second cooling mode, the thermal adjustment device may use a 21° C. threshold. As another example, in a third cooling mode, the thermal adjustment device may use a 20° C. threshold. It should be understood that, as used herein, a temperature measurement may refer to a temperature measurement associated with a heat pump. For example, the thermal adjustment device may measure a temperature of a thermal conductor (e.g., a heatsink, etc.) in thermal communication with a heat pump (e.g., Peltier, etc.). As another example, the thermal adjustment device may measure a temperature of a surface of the heat pump.

Referring now specifically to FIGS. 3D-3F, in first stage 360, the thermal adjustment device may apply a first voltage to the heat pump for a set time period (e.g., 20 second, 40 seconds, etc.) and/or until a temperature threshold is met. In second stage 370, the thermal adjustment device may apply a second voltage to the heat pump and may adjust the second voltage based on monitoring a temperature of a surface of the thermal adjustment device (e.g., to achieve a temperature setpoint, to ensure a safe surface temperature for the user, etc.).

In first stage 360, the thermal adjustment device may apply a first voltage to the heat pump (thereby causing a surface in thermal communication with a user to warm) for a time period (e.g., 20 seconds). If the temperature of the surface is higher than a threshold (e.g., 38° C., etc.), the thermal adjustment device may transition to second stage 370. Additionally or alternatively, at the end of the time period, the thermal adjustment device may transition to second stage 370.

In second stage 370, the thermal adjustment device may apply a second voltage (e.g., 1.75V, etc.) to the heat pump. The thermal adjustment device may monitor a temperature of the surface periodically (e.g., every 4 seconds, etc.). In response to a temperature of the surface, the thermal adjustment device may perform an action (e.g., adjust an input voltage to the heat pump, etc.). In various embodiments, the thermal adjustment device implements the function.

IF (temperature<threshold (e.g., 39.5° C.))→increase a voltage of the variable input by step size (e.g., 0.05V)

IF (temperature threshold (e.g., 46° C.))→set a voltage of the variable input to a value (e.g., 0.0V)

It should be understood that other temperature thresholds, voltage adjustments (e.g., steps of 1V, 2V, etc.), and/or variable input values (e.g., 0.01V, etc.) are possible. Moreover, it should be understood that the thresholds may be the same and/or different. For example, the thermal adjustment device may utilize a first threshold as a setpoint and a second threshold as a safe operating temperature ceiling. The thermal adjustment device may implement one or more safe temperature routines. For example, a first routine may determine whether a temperature of a surface of the thermal adjustment device is outside a first range (e.g., 15 degrees Centigrade to 49 degrees Centigrade, etc.) and a second routine may determine whether a temperature of the surface is outside a second range (e.g., 10 degrees Centigrade to 50 degrees Centigrade, etc.). In some embodiments, the one or more routines are executed by different components of the thermal adjustment device (e.g., to provide redundancy, etc.). For example, a first processor may execute a first routine and a second processor may execute a second routine. In some embodiments, the thermal adjustment device implements one or more temperature monitoring routines. For example, a first routine may determine whether a temperature of a surface of the thermal adjustment device is outside a safe temperature range for a user (e.g., 10 degrees Centigrade to 50 degrees Centigrade) and a second routine may determine whether a temperature of the surface of the thermal adjustment device is outside a temperature range associated with a current operating mode (e.g., 41.5 degrees Centigrade to 46 degrees Centigrade for a third heating mode, etc.).

Figure 3G:
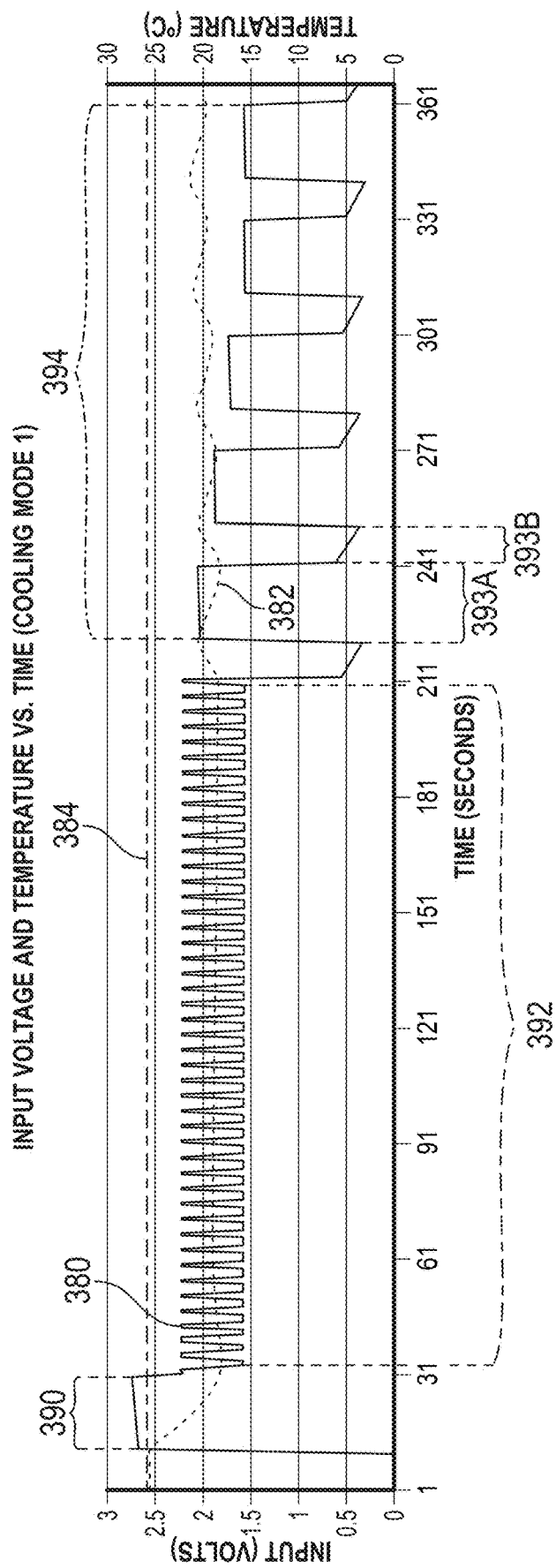
Figure 3H:
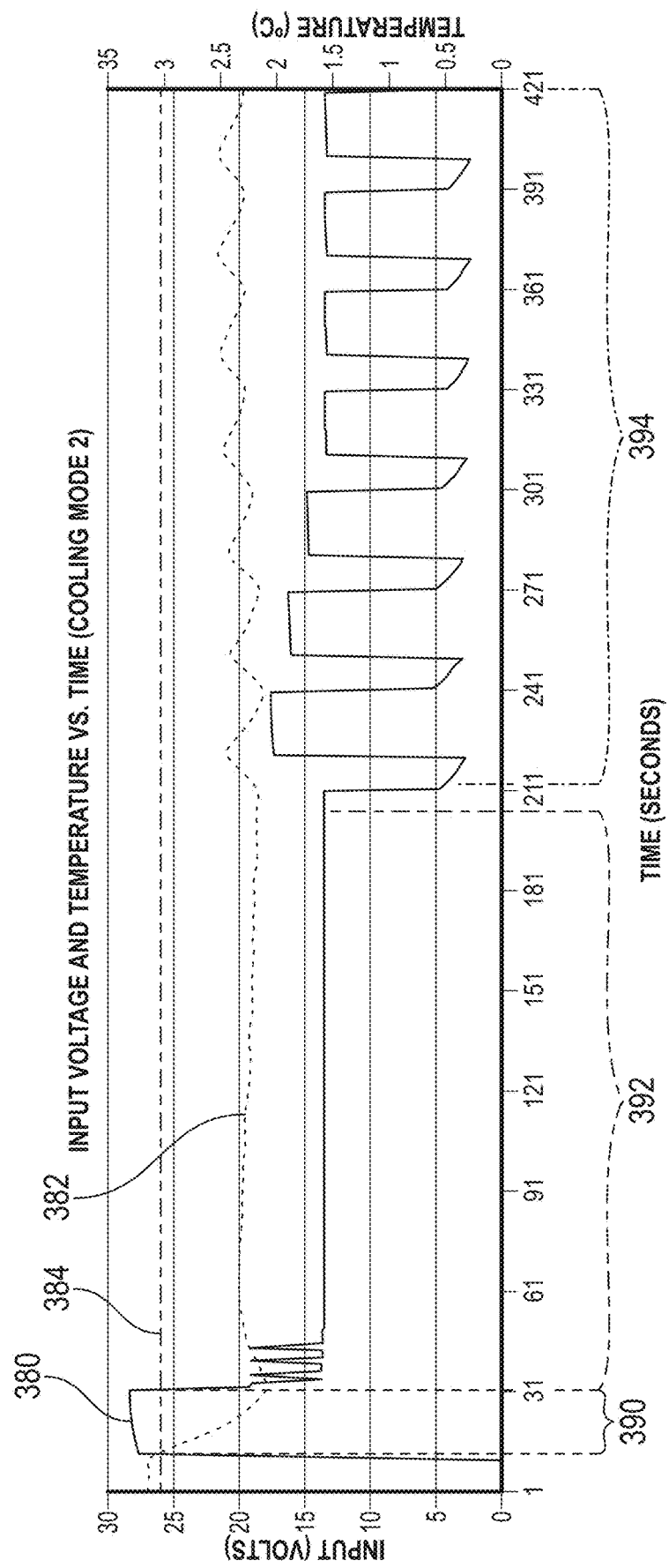
Figure 3I:
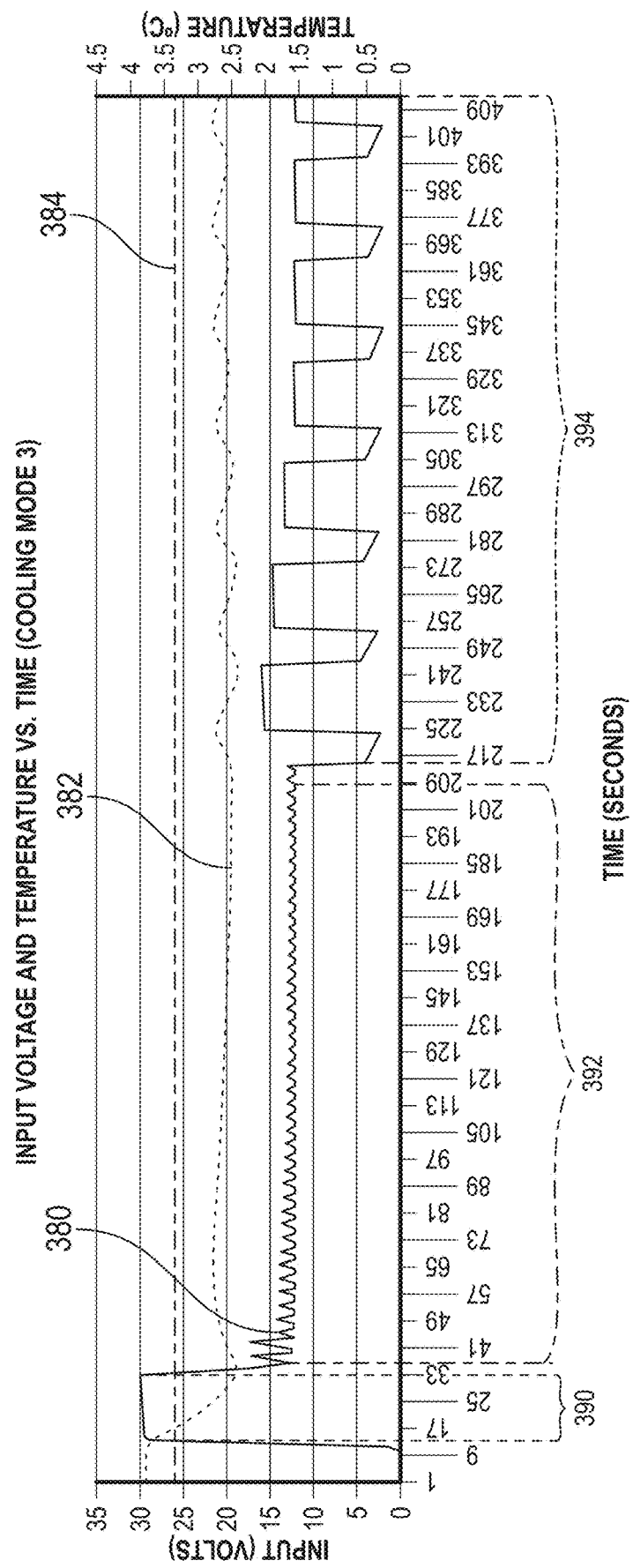
Figure 3J:
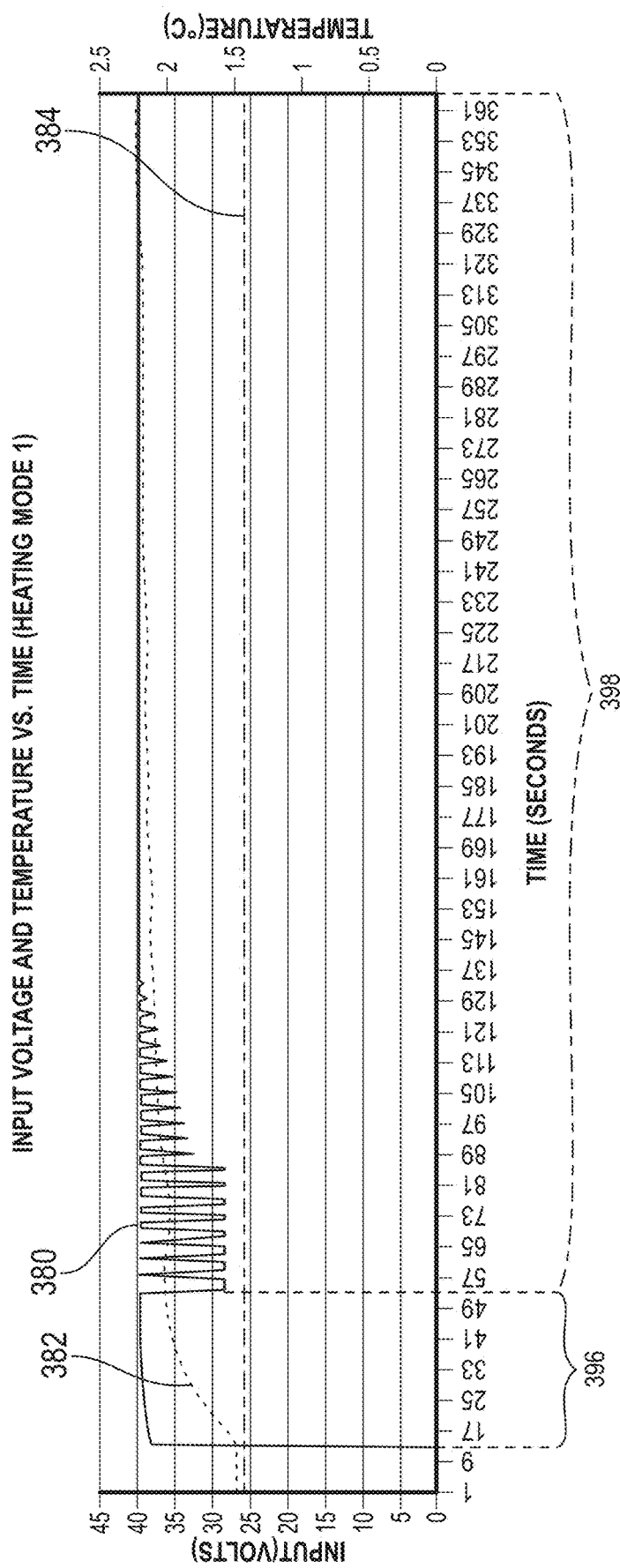
Figure 3K:
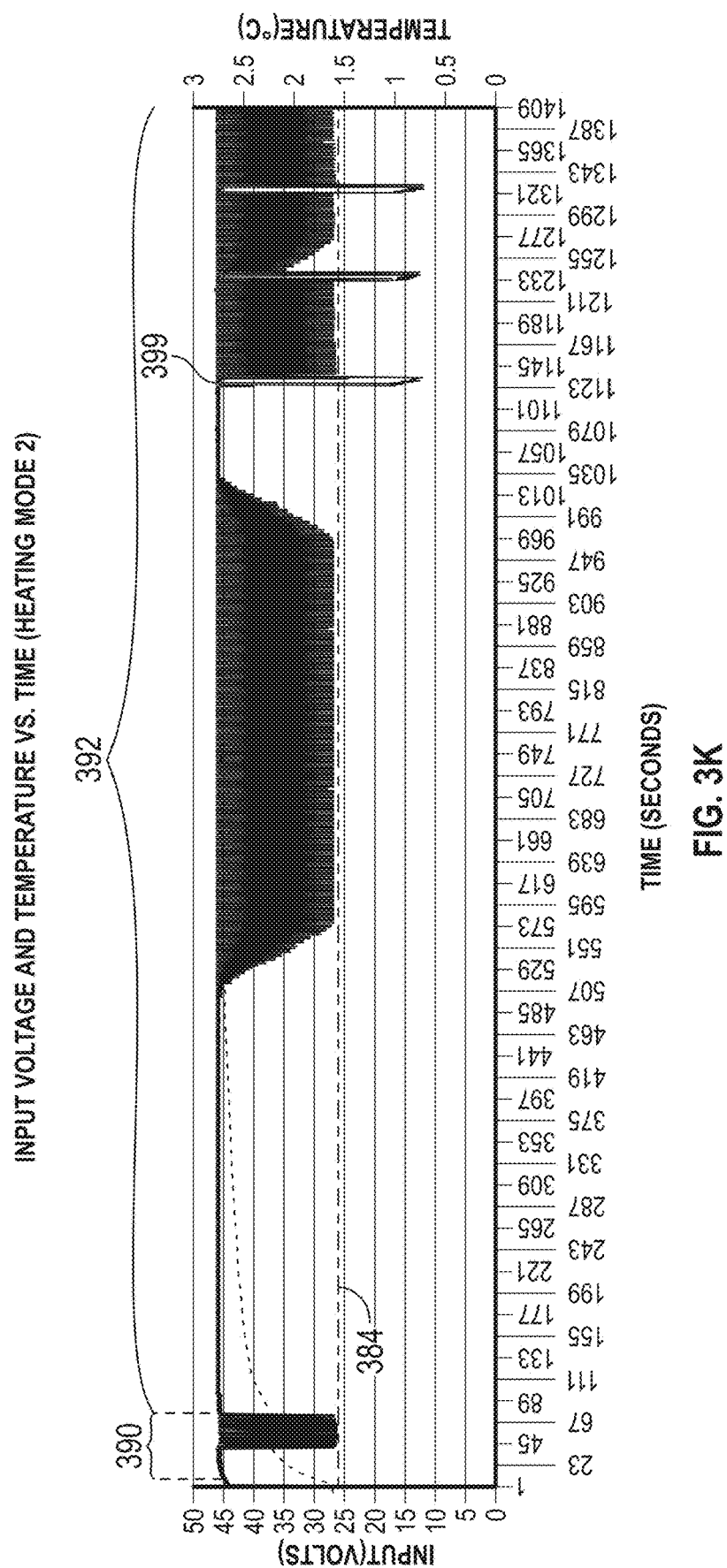
Figure 3L:
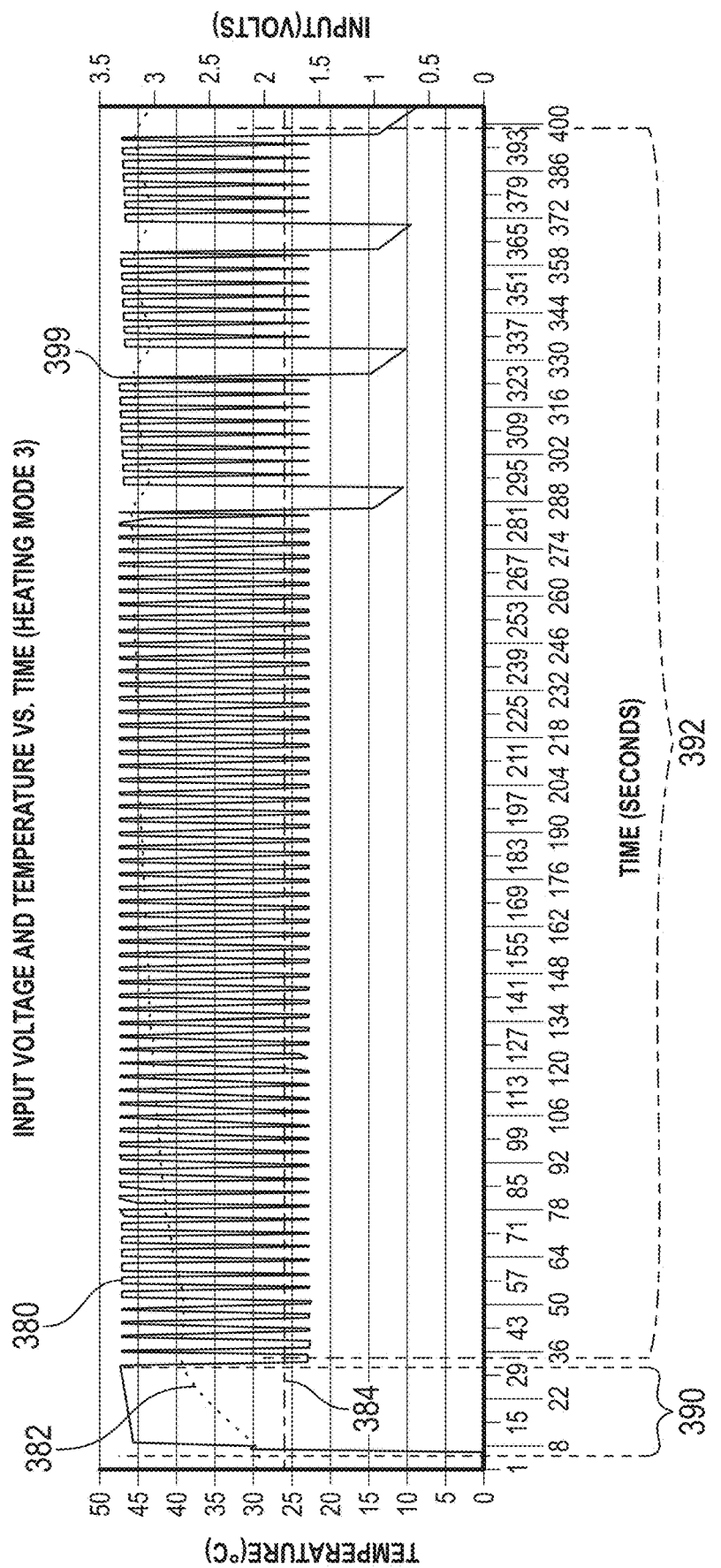

Referring now specifically to FIGS. 3G-3L, input voltage 380 associated with temperature 382 is shown, according to an exemplary embodiment. In various embodiments, the thermal adjustment device applies input voltage 380 to a heat pump (e.g., a Peltier, etc.) to achieve temperature 382 (given ambient temperature 384) at a surface of the heat pump (e.g., a surface in thermal communication with a user, etc.). As shown, FIGS. 3G-3I include first stage 390, second stage 392, and third stage 394. However, it should be understood that the thermal adjustment device may implement greater/fewer stages. Each stage may correspond to a different functionality. For example, first stage 390 corresponds to a cooling initialization stage and may include applying a static input to the heat pump. As another example, second stage 392 corresponds to a cooling stabilization stage and may include applying a dynamic input (e.g., an input that changes in response to one or more conditions such as a temperature measurement, etc.) to the heat pump. As another example, third stage 394 corresponds to a waved cooling stage and may include applying a variable input. In various embodiments, the variable input includes powered period 393A and unpowered period 393B. Powered period 393A may correspond to a time period (e.g., 20 seconds, etc.) during which the thermal adjustment device applies a first voltage to the heat pump. Unpowered period 393B may correspond to a time period (e.g., 10 seconds, etc.) during which the thermal adjustment device applies a second voltage to the heat pump. In various embodiments, the first voltage is greater than the second voltage. For example, the first voltage may be 2.6 Volts and the second voltage may be 0.25 Volts. In some embodiments, the first voltage is dynamic (e.g., changes in response to one or more conditions such as a temperature measurement). For example, the thermal adjustment device applies 2.6 Volts to the heat pump, measures a temperature of a surface of the heat pump, and in response determining whether the surface corresponds to a safe operating temperature for a user (e.g., based on the temperature measurement), applies 2.4 Volts to the heat pump. In some embodiments, the second voltage is zero (or substantially close to zero). In various embodiments, each stage is associated with a different input to the heat pump (as described in greater detail with reference to FIG. 2, above). FIG. 3G corresponds to a first cooling mode (e.g., low cooling intensity). FIG. 3H corresponds to a second cooling mode (e.g., medium cooling intensity). FIG. 3I corresponds to a third cooling mode (e.g., high cooling intensity). FIG. 3J corresponds to a first heating mode (e.g., low heating intensity). FIG. 3K corresponds to a second heating mode (e.g., medium heating intensity). FIG. 3L corresponds to a third heating mode (e.g., high heating intensity).

As shown, FIGS. 3J-3L include first stage 396 and second stage 398. First stage 396 may correspond to a heating initialization stage and may include applying a static input to the heat pump. Second stage 398 may correspond to a heating stabilization stage and may include applying a dynamic input (e.g., an input that changes in response to one or more conditions such as temperature, etc.) to the heat pump. FIG. 3J corresponds to a first heating mode (e.g., low heating intensity). FIG. 3K corresponds to a second heating mode (e.g., medium heating intensity). FIG. 3J corresponds to a third heating mode (e.g., high heating intensity). The thermal adjustment device may transition between the stages described in FIGS. 3G-3L in response to one or more conditions such as time and/or temperature (e.g., a temperature measurement corresponding to a surface of a heat pump, etc.). In various embodiments, the thermal adjustment device transitions between the modes described in FIGS. 3G-3L in response to a user input (e.g., a user selecting an operating mode using a user interface of the thermal adjustment device, etc.).

Figure 4:
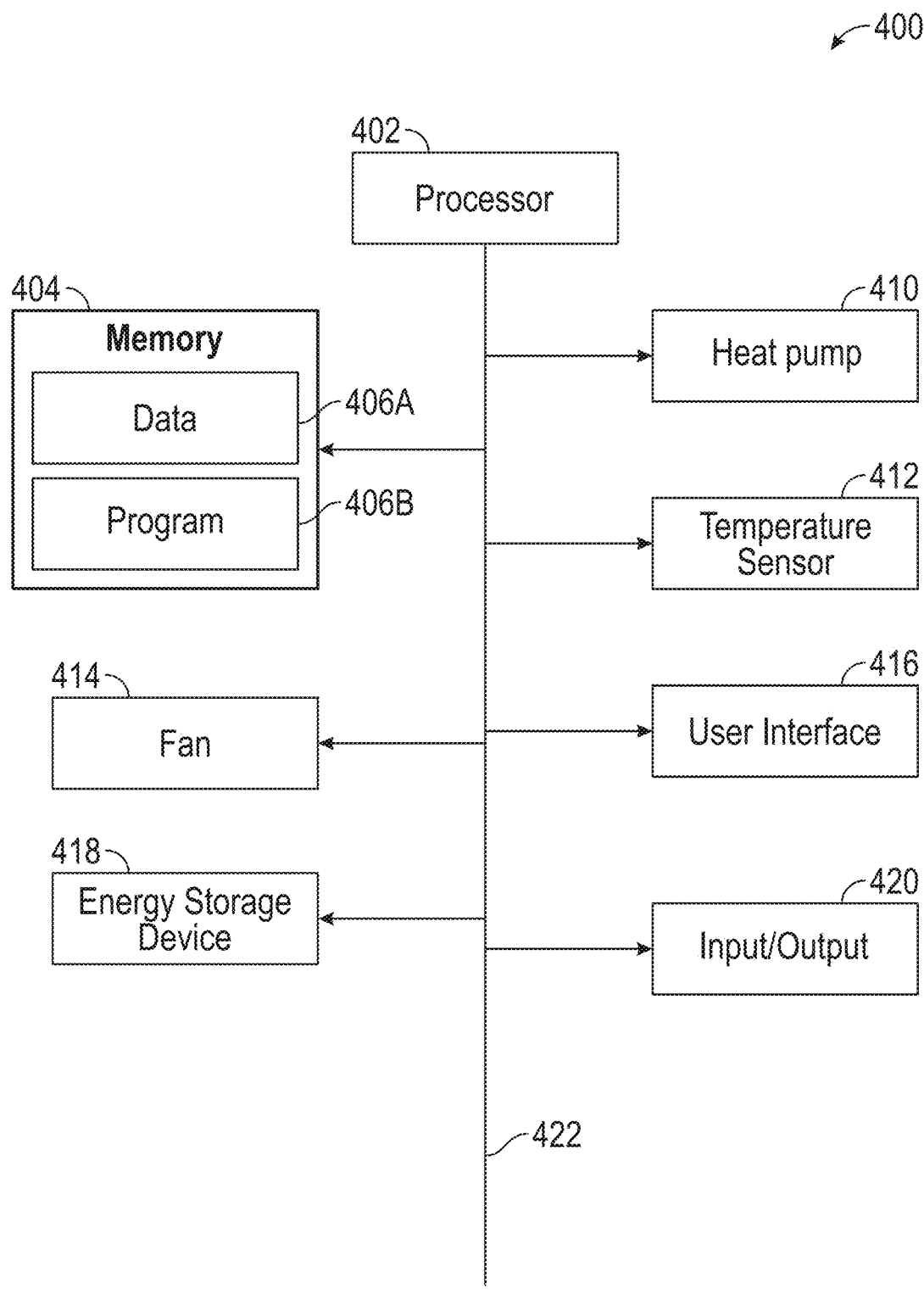
FIG. 4 illustrates a block diagram of a thermal adjustment device, in accordance with an embodiment.

Referring now to FIG. 4, thermal adjustment device 400 is shown, according to an exemplary embodiment. Thermal adjustment device 400 may be used by a user to provide a comfortable temperature. For example, thermal adjustment device 400 may be used to heat and/or cool a user. In some embodiments, thermal adjustment device 400 includes processor 402, memory 404, heat pump 410, temperature sensor 412, fan 414, user interface 416, energy storage device 418 and/or input/output 420. Elements of thermal adjustment device 400 may be connected with communication link 422. In various embodiments, communication link 422 is wired. For example, communication link 422 may include a wired bus. It should be understood that the components of thermal adjustment device 400 can be connected in any suitable manner, such as via a physical bus, or wirelessly.

Processor 402 may include hardware for executing instructions, such as those making up a computer program. As an example and not by way of limitation, to execute instructions, processor 402 may retrieve (or fetch) the instructions from an internal register, an internal cache, memory 404; decode and execute them; and then write one or more results to an internal register, an internal cache, or memory 404. Processor 402 may include one or more internal caches for data, instructions, or addresses.

Memory 404 can be any suitable device that provides storage, such as an electrical, magnetic, or optical memory including a RAM, cache, hard drive, or removable storage disk. In some embodiments, memory 404 includes data 406A and program 406B. Data 406A and/or program 408B may store instructions to cause processor 402 to perform the methods disclosed herein. In particular embodiments, memory 404 includes main memory for storing instructions (e.g., program 406B) for processor 402 to execute or data 406A for processor 402 to operate on. In particular embodiments, one or more memory management units (MMUs) reside between processor 402 and memory 404 and facilitate accesses to memory 404 requested by processor 402. In particular embodiments, memory 404 includes random access memory (RAM). This disclosure contemplates any suitable RAM.

Program 406B can be stored and/or transported within any non-transitory, computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as memory 404, that can contain or store programming for use by or in connection with an instruction-execution system, apparatus, or device.

Program 406B can also be propagated within any transport medium for use by or in connection with an instruction-execution system, apparatus, or device, such as those described above, that can fetch instructions associated with the software from the instruction-execution system, apparatus, or device and execute the instructions. In the context of this disclosure, a transport medium can be any medium that can communicate, propagate, or transport programming for use by or in connection with an instruction-execution system, apparatus, or device. The transport readable medium can include, but is not limited to, an electronic, magnetic, optical, electromagnetic, or infrared wired or wireless propagation medium.

Heat pump 410 may transfer heat from a first side of heat pump 410 to a second side of heat pump 410. It should be understood that while heat pump 410 is described as a heat pump, it may be or include any thermoelectric heat pump. For example, heat pump 410 may include a Peltier. Heat pump 410 may include one or more components. For example, heat pump 410 may include a Peltier coupled between a heat conducting plate (e.g., a thermal mass, etc.) and a heatsink. In various embodiments, thermal adjustment device 400 operates heat pump 410 via one or more inputs. For example, thermal adjustment device 400 may apply a first voltage to an input of heat pump 410 to cause heat pump 410 to transfer heat from a first surface to a second surface (e.g., cool the first surface). To continue the previous example, thermal adjustment device 400 may apply a second voltage (e.g., having an opposite polarity as the first voltage) to an input of heat pump 410 to cause heat pump 410 to transfer heat from the second surface to the first surface (e.g., heat the second surface). In various embodiments, heat pump 410 includes one or more surfaces. For example, heat pump 410 may include a first surface on a first side of heat pump 410 configured to be positioned in thermal communication with a user's skin and a second surface on a second side of heat pump 410 configured to be positioned in thermal communication with a heatsink/radiator. In some embodiments, a surface area of the one or more surfaces is greater than traditional thermal adjustment devices. In some embodiments, the surface (e.g., a surface in thermal communication with a user) is sized to fit a user. For example, the surface may be sized to fit between a user's shoulder blades (e.g., the surface may be 2.36 inches across, etc.). As another example, the surface may be 55.5 millimeters (e.g., in width) by 60 millimeters (e.g., in length). Advantageously, by including a larger surface area, thermal adjustment device 400 may increase heat transfer with a thermal mass (e.g., a user's skin) while remaining sizable to a user (e.g., not too large to fit between the user's shoulder blades, etc.). Moreover, a surface of heat pump 410 may include a larger thermal mass than traditional thermal adjustment devices. Advantageously, by including a larger thermal mass, thermal adjustment device 400 may more effectively heat/cool a thermal mass in communication with heat pump 410 (e.g., a user's skin).

In various embodiments, thermal adjustment device 400 receives information from temperature sensor 412. Temperature sensor 412 may be and/or include any system/device configured to capture temperature information. For example, temperature sensor 412 may include a thermometer, a therm, a thermistor, a thermocouple, a resistance thermometer, a silicon bandgap temperature sensor, an infrared thermometer, a fiber-optic thermometer, a DTS system, a pyrometer, and/or the like.

Fan 414 may facilitate ambient air heat transfer for one or more components of thermal adjustment device 400. For example, fan 414 may draw in ambient air to heat and/or cool a surface of heat pump 410. In various embodiments, fan 414 draws in air from an ingress portion of thermal adjustment device 400 (e.g., an intake, etc.) and expels the air from an egress portion of thermal adjustment device 400 (e.g., an exhaust, etc.). Fan 414 may be or include a direct-current (DC) brushless blower. In some embodiments, fan 414 operates during a cooling mode. Additionally or alternatively, fan 414 may operate during a heating mode. In various embodiments, thermal adjustment device 400 operates fan 414 based on one or more operating parameters (e.g., a temperature of a heat pump, an ambient temperature, etc.). In various embodiments, the ingress and/or egress portions of thermal adjustment device 400 include a structure to prevent particulate matter, hair, etc. from entering thermal adjustment device 400. For example, thermal adjustment device 400 may include an ingress portion having two layers of vents (e.g., a first horizontal layer and a second layer including a number of holes, etc.) that are offset to prevent a user's hair from ingress into thermal adjustment device 400.

In various embodiments, a user operates thermal adjustment device 400 via user interface 416. User interface 416 may be configured to receive an input from a user (e.g., a touch input, a button input, a voice input), and a setting of thermal adjustment device 400 may be updated in response to receiving the input from the user (e.g., to change between heating and cooling modes, to change a temperature setpoint, etc.). User interface 416 may include a button, a switch, a slider, a dial, and/or the like. In various embodiments, user interface 416 includes a display element. For example, user interface 416 may include one or more light-emitting diodes (LEDs) that indicate a current heating/cooling mode of thermal adjustment device 400. As another example, user interface 416 may include a number of LEDs to indicate a battery charge.

Energy storage device 418 may store energy to power thermal adjustment device 400. In various embodiments, energy storage device 418 includes a battery. Energy storage device 418 may be integral to thermal adjustment device 400. Additionally or alternatively, energy storage device 418 may be positioned remotely of thermal adjustment device 400. For example, thermal adjustment device 400 may include a power cord that connects to an external battery bank. In various embodiments, energy storage device 418 may have a greater energy capacity than traditional thermal adjustment devices. For example, energy storage device 418 may have an energy capacity sufficient to operate thermal adjustment device 400 for 4 hours (e.g., in a specific heating/cooling mode, etc.). Additionally or alternatively, thermal adjustment device 400 may facilitate higher current levels between energy storage device 418 and heat pump 410 than traditional thermal adjustment devices. Advantageously, by including a greater energy capacity/current levels, thermal adjustment device 400 may operate a heat pump using larger power inputs (e.g., voltage, current, etc.), thereby facilitating a comfortable personal temperature (e.g., because of a greater ability to quickly heat/cool heat pump 410, etc.).

Input/output 420 may include one or more interfaces. For example, thermal adjustment device 400 may include a universal serial bus (USB) type C connection to facilitate charging energy storage device 418.

Referring now generally to FIGS. 5A-5H, thermal adjustment device 500 and lanyard 600 are shown, in accordance with an embodiment. In brief, thermal adjustment device 500 may couple within lanyard 600 and be worn by a user to position a surface of thermal adjustment device 500 in thermal communication with the user's skin. For example, lanyard 600 positions thermal adjustment device 500 on a user's upper back such that a heat pump of thermal adjustment device 500 directly contacts the user's skin. Additionally or alternatively, the heat pump may indirectly contact a user (e.g., be separated by a layer of material such as an undershirt, etc.). In various embodiments, thermal adjustment device 500 is a personal air-conditioning (AC) device.

Figure 5A:
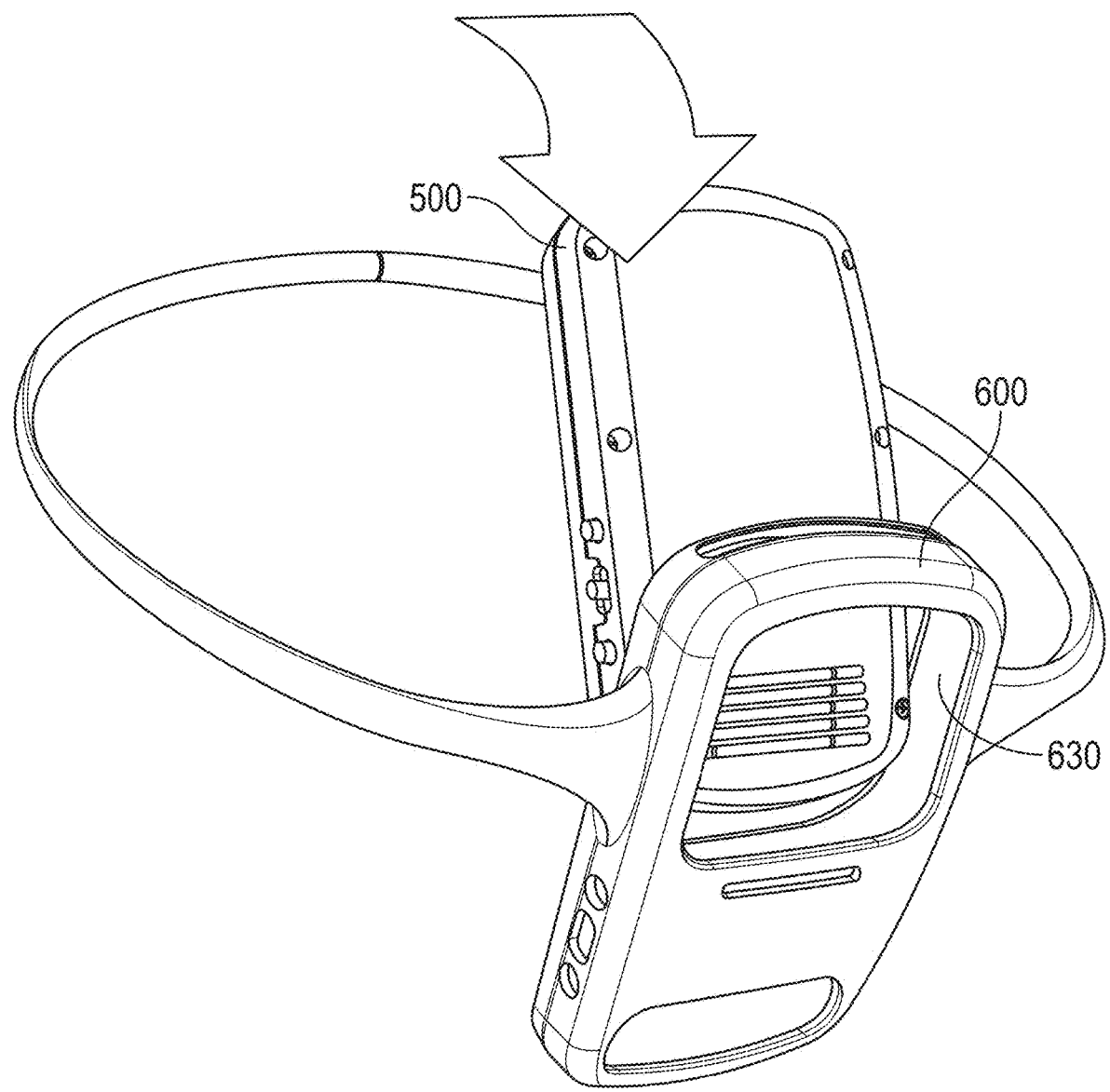
FIGS. 5A and 5B illustrate an exemplary thermal adjustment device and lanyard, in accordance with an embodiment.
Figure 5B:
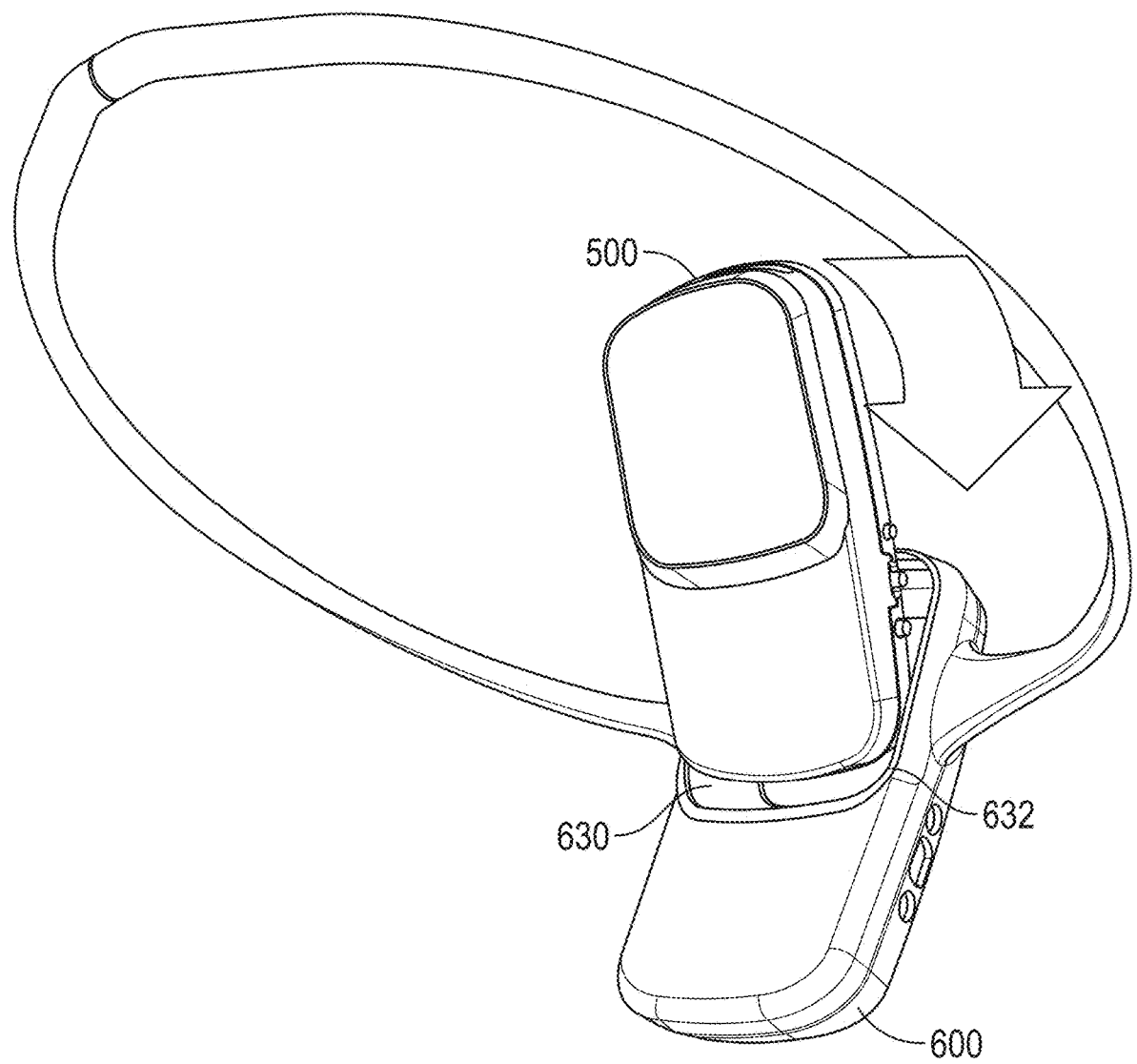

FIGS. 5A and 5B illustrate an exemplary thermal adjustment device 500 and lanyard 600, in accordance with an embodiment. As shown in FIGS. 5A and 5B, thermal adjustment device 500 is inserted into pocket 630 of lanyard 600. Pocket 630 may be or include a volume within lanyard 600 to receive thermal adjustment device 500. Pocket 630 may at least partially surround thermal adjustment device 500 to secure thermal adjustment device 500 within pocket 630. In some embodiments, a size (e.g., volume, dimensions, etc.) of pocket 630 (e.g., pocket 630 without thermal adjustment device 500 inserted, etc.) is different than a size of thermal adjustment device 500. For example, pocket 630 may be smaller than thermal adjustment device 500 (e.g., 0.5% smaller in scale than thermal adjustment device 500, etc.) to facilitate a secure fit of thermal adjustment device 500 within pocket 630 (e.g., via friction). In some embodiments, one or more components of thermal adjustment device 500 mechanically couple with lanyard 600 to facilitate a secure fit of thermal adjustment device 500 within pocket 630. For example, while inserting thermal adjustment device 500 into pocket 630, a user may stretch lanyard 600 around thermal adjustment device 500 such that controls 520 mechanically couple within a user interface portion 620, thereby securing thermal adjustment device 500. As another example, pocket 630 may include a raised portion (shown as lip 802 in FIG. 8A) to facilitate a mechanical connection with surface 540. In various embodiments, pocket 630 is shaped substantially similarly to thermal adjustment device 500. For example, thermal adjustment device 500 may have an outer curvature and pocket 630 may include the curvature to facilitate a secure fit of thermal adjustment device 500. Pocket 630 includes a skin contact opening (shown as opening 632) into which thermal adjustment device 500 is positioned. When positioned in pocket 630, lanyard 600 may provide a protective case for thermal adjustment device 500. In some embodiments, opening 632 is larger than surface 540. For example, opening 632 may have a radius that is 1.5 millimeters less than a radius of surface 540. In various embodiments, a size of opening 632 is less than thermal adjustment device 500 (e.g., to prevent thermal adjustment device 500 from passing through opening 632 without user intervention such as stretching lanyard 600 around thermal adjustment device 500). Pocket may include a number of openings (e.g., first aperture 612, second aperture 614, third aperture 616, etc.) to facilitate operation of thermal adjustment device 500. In some embodiments, the number of openings facilitate heat transfer between thermal adjustment device 500 and the ambient environment (e.g., when in a cooling mode, etc.). In some embodiments, pocket 630 is ergonomic and/or hypoallergenic, at least in portions that contact a user's skin. Pocket 630, in some embodiments, extends further in the region of controls 520 (e.g., shown in FIG. 5H) of thermal adjustment device 500, thereby providing additional protection of controls 520.

As shown in FIG. 5A, pocket 630 also includes transparent strip 618. Strip 618 allows for operational LEDs, positioned on/integrated within thermal adjustment device 500, to be visible to a user when thermal adjustment device 500 is positioned in pocket 630. In various embodiments, the LEDs may be occluded from a user (e.g., not visible to the user) when off. Strip 618 may be or include a thin layer of material (e.g., silicon, etc.) that allows light from the LEDs to be viewed by a user. The LEDs may provide operational information to the user (e.g., battery level, current operating mode, etc.).

Figure 5C:
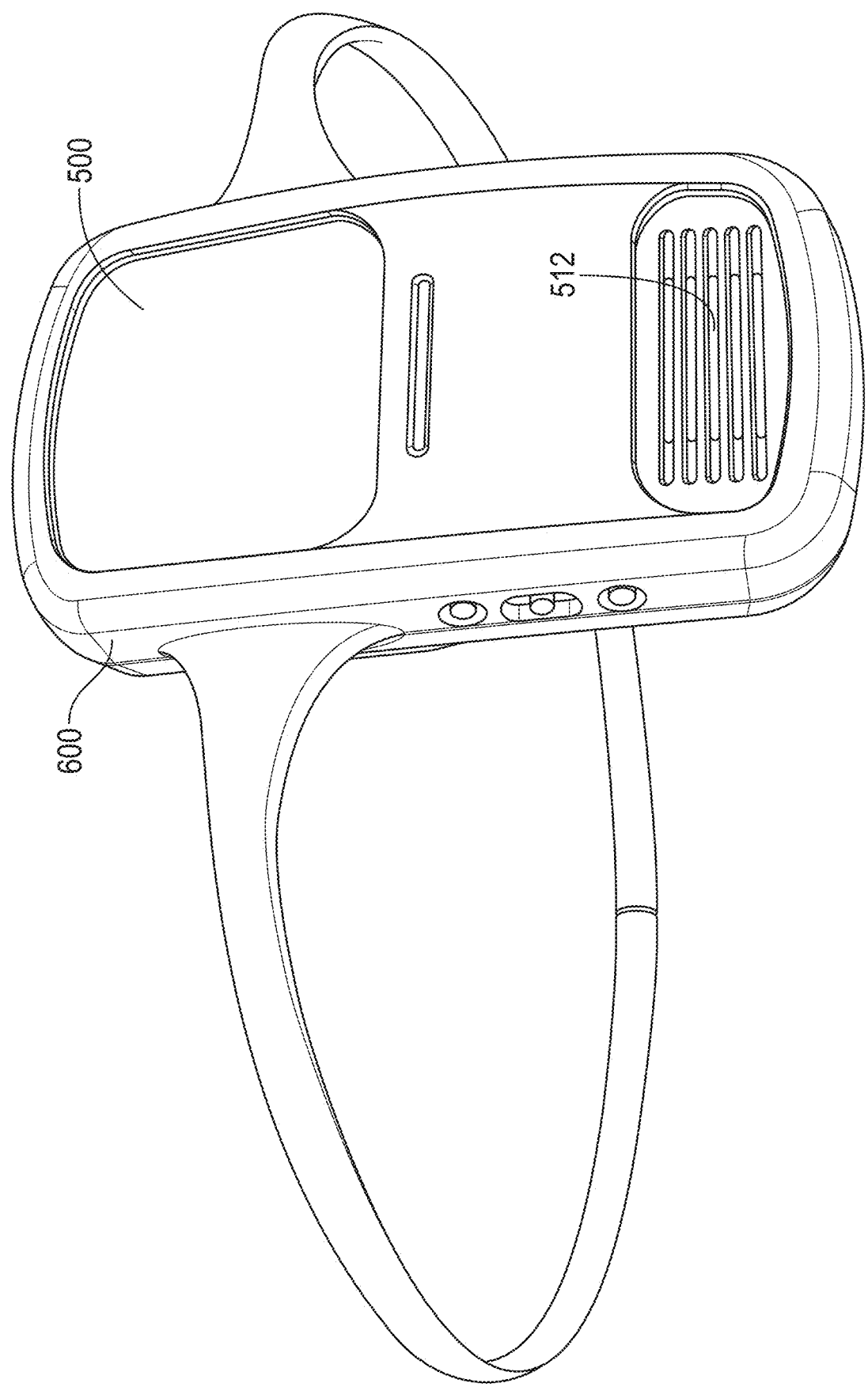
FIGS. 5C-5E illustrate various perspectives of an exemplary thermal adjustment device inserted into a lanyard, in accordance with an embodiment.
Figure 5D:
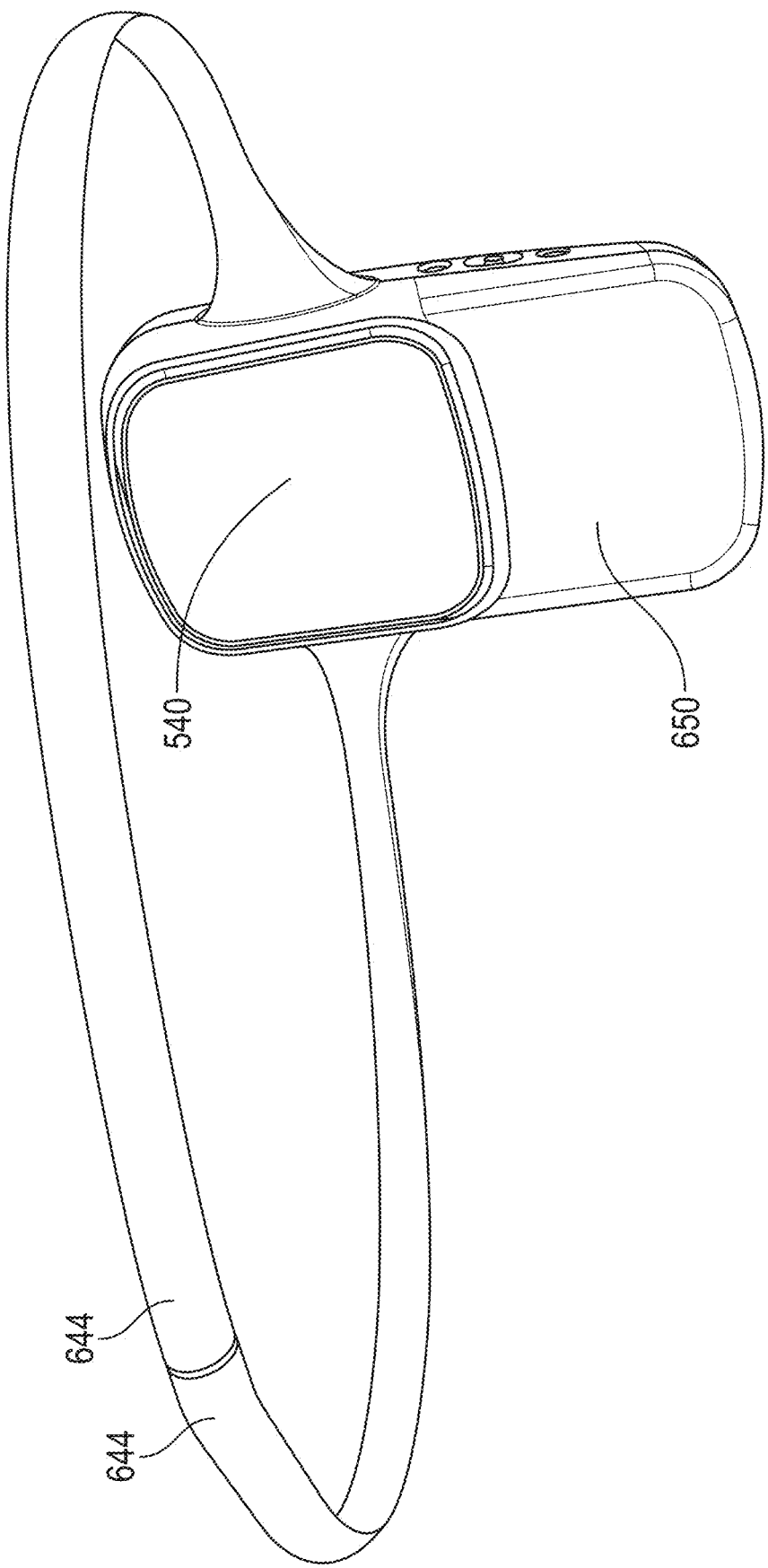
Figure 5E:
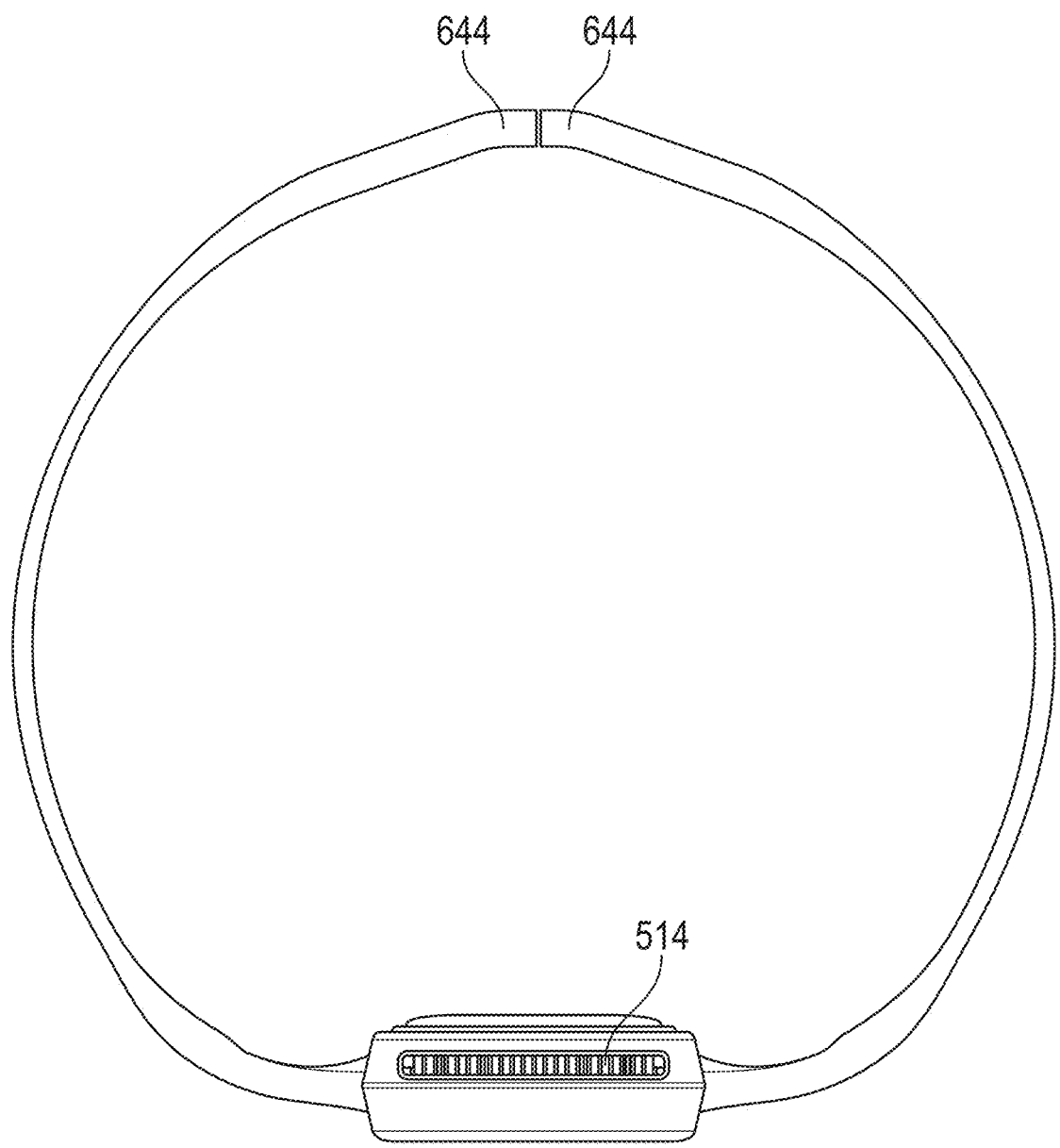
Figure 5F:
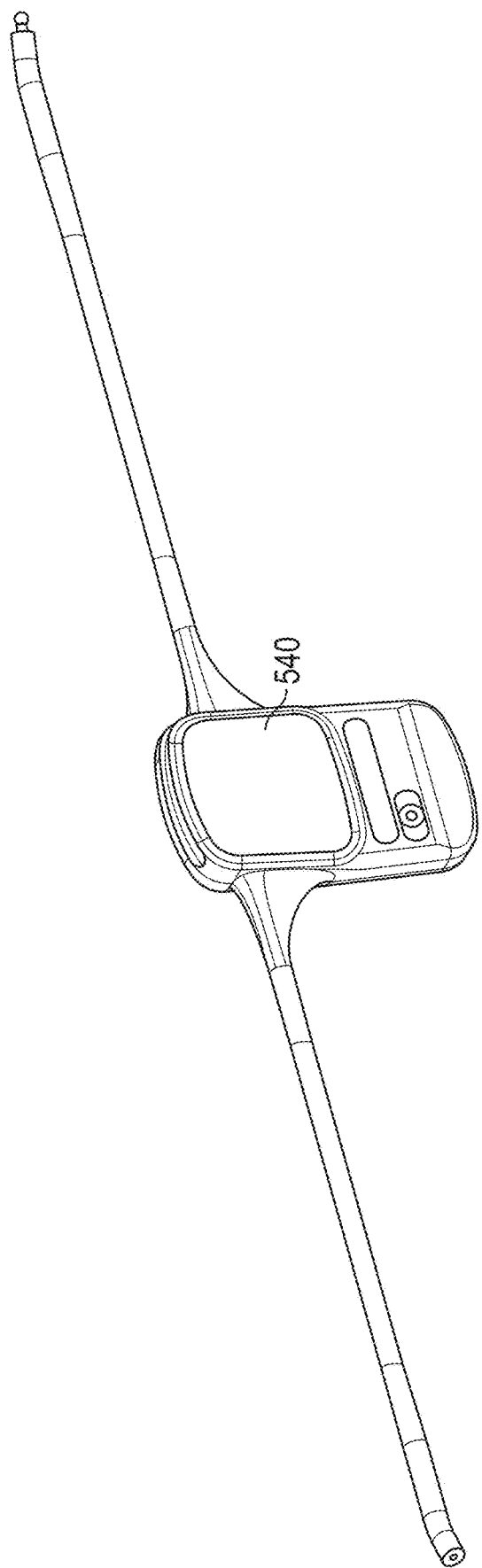
FIG. 5F illustrates an exemplary thermal adjustment device coupled to a lanyard, in accordance with an embodiment.
Figure 5G:
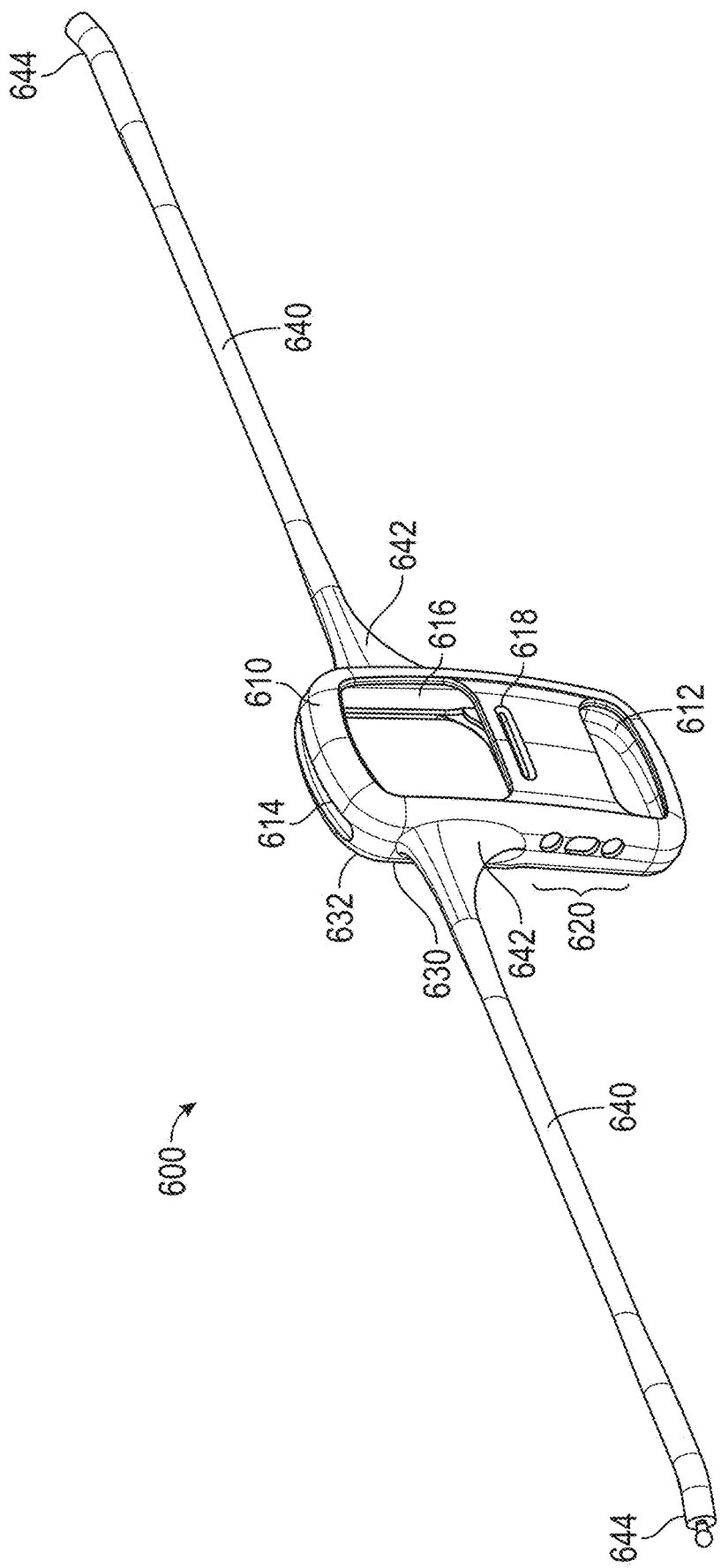
FIG. 5G illustrate an exemplary lanyard for a thermal adjustment device, in accordance with an embodiment.

FIGS. 5C-5E illustrate various perspectives of an exemplary thermal adjustment device 500 inserted into lanyard 600, in accordance with an embodiment. The lanyard's arms (shown as arms 640) may include a clasp (shown as fastener 644) opposite pocket 630 to fix the arms around a neck of a user (see FIGS. 6A-6C below). In some embodiments, the clasp is a magnetic clasp or a ball and socket clasp (unclasped arms are illustrated in FIGS. 5F and 5G below). As shown in FIG. 5D, thermal adjustment device 500 includes a heat transfer plate (shown as surface 540) that contacts the user skin for heating and/or cooling. In various embodiments, lanyard 600 exposes the heat transfer plate of thermal adjustment device 500. For example, lanyard 600 may insulate thermal adjustment device 500 while exposing the heat transfer plate to allow a user to position the heat transfer plate in thermal communication with their skin (e.g., while insulating other portions of the thermal adjustment device from the user's skin). Additionally or alternatively, lanyard 600 may protect thermal adjustment device 500 from impact. For example, lanyard 600 may protect thermal adjustment device 500 from damage if dropped. In various embodiments, the heat transfer plate is constructed of a thermally conductive material (e.g., a metal, etc.).

FIG. 5F illustrates an exemplary thermal adjustment device 500 coupled to lanyard 600, in accordance with an embodiment. In the configuration illustrated in FIG. 5F, lanyard 600 is unclasped and thermal adjustment device 500 is positioned in pocket 630 of lanyard 600. FIG. 5G illustrates lanyard 600 of FIG. 5F with thermal adjustment device 500 removed. Lanyard 600 may include body 610 coupled to arms 640 via trusses 642. In various embodiments, body 610 includes an internal pocket to receive thermal adjustment device 500 (shown as pocket 630). Body 610 is shown to include first aperture 612, second aperture 614, third aperture 616, strip 618, and user interface portion 620.

Advantageously, lanyard 600 may include one or more apertures (e.g., holes, shown as first aperture 612 and second aperture 614, etc.) to facilitate airflow to the thermal adjustment device. For example, pocket 630 of lanyard 600 may include one or more holes that may allow airflow to thermal adjustment device 500 (e.g., to facilitate heat transfer with a thermal heat pump such as a heat pump, etc.). User interface portion 620 may be or include an aperture that facilitates user operation of user interface 520. For example, user interface portion 620 may include a hole in body 610 that allows a user to interact with one or more buttons, switches, sliders, dials, and/or the like of thermal adjustment device 500.

Figure 5H:
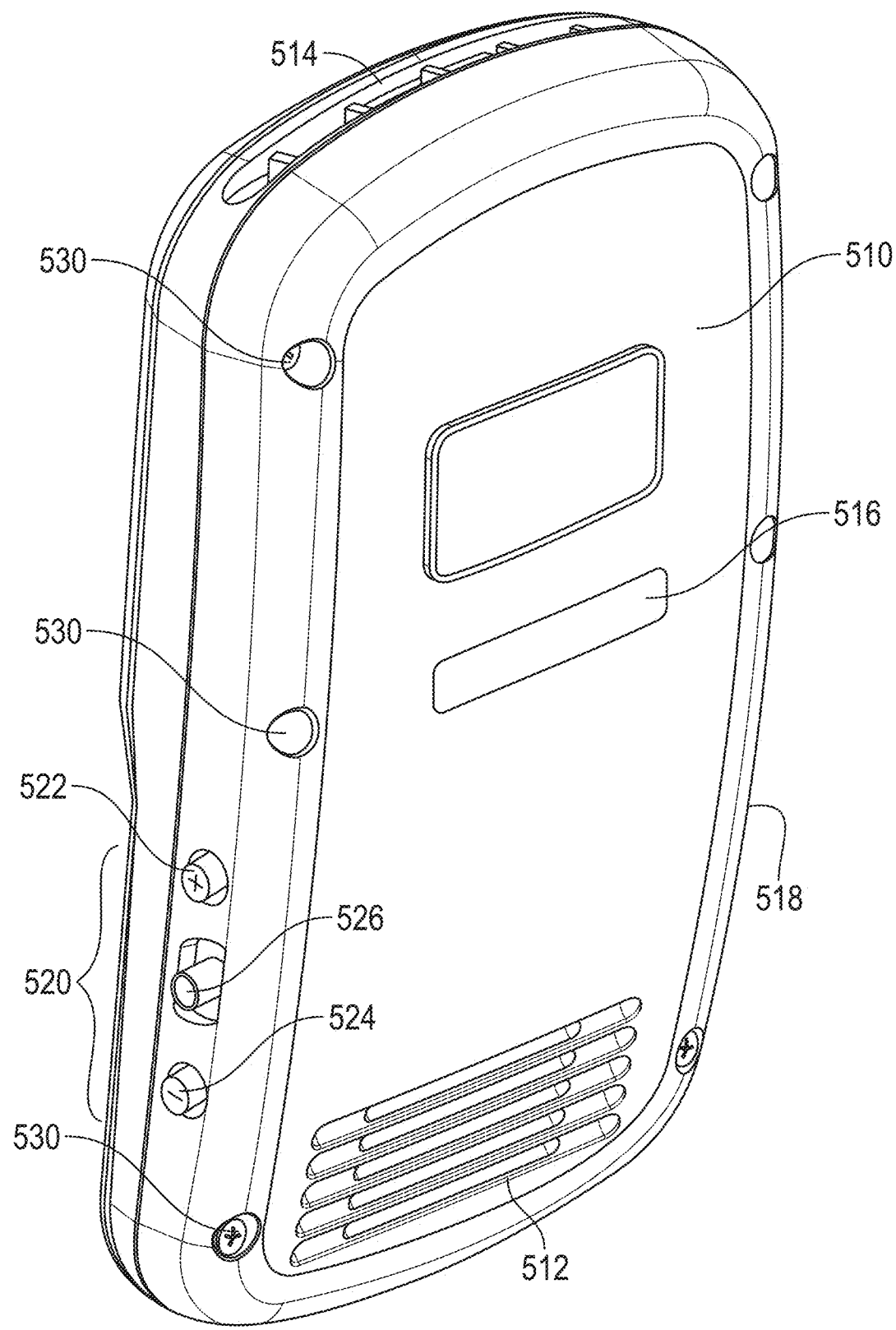
FIG. 5H illustrates an exemplary thermal adjustment device, in accordance with an embodiment.

FIG. 5H illustrates the exemplary thermal adjustment device 500 without lanyard 600, in accordance with an embodiment. Thermal adjustment device 500 may include body 510, intake 512, exhaust 514, display 516, input/output 518, user interface 520, and/or fastener(s) 530. Body 510 may be or include a case. For example, body 510 may include a plastic case that houses components of thermal adjustment device 500 (e.g., processor 402, memory 404, heat pump 410, temperature sensor 412, fan 414, user interface 416, energy storage device 418, and/or input/output 420, etc.). Intake 512 may be or include an air intake to facilitate heat transfer with one or more components of thermal adjustment device 500. For example, intake 512 may include a number of holes to allow a fan of thermal adjustment device to draw in air (via intake 512) and expel the air (via exhaust 514), thereby reducing heat buildup associated with a heat pump during a cooling mode. In various embodiments, intake 512 and/or exhaust 514 include one or more features (shown as first protective feature 513A and second protective feature 513B) to prevent particulate ingress. For example, intake 512 may include a first and second layer of apertures (e.g., slits, holes, etc.) that are aligned to prevent a user's hair from entering into thermal adjustment device 500 (e.g., where the hair could interact with a fan of the thermal adjustment device, etc.). As another example, exhaust 514 may include a grille (as show in FIG. 5E) to prevent particulate ingress. In some embodiments, the grille improves exhaust air flow (e.g., by reducing turbulent airflow, by encouraging laminar airflow, etc.). In some embodiments, first protective feature 513A include one or more horizontal slits (e.g., slits in body 510). In some embodiments, second protective feature 513B includes a surface having one or more holes. Second protective feature 513B may be positioned between first protective feature 513A and a fan (shown as fan 560 in FIG. 5I). In various embodiments, first protective feature 513A and second protective feature 513B are aligned such that particulate (e.g., hair, etc.) must pass through first protective feature 513A and second protective feature 513B before contacting an internal component (e.g., a fan, etc.) of thermal adjustment device 500. In some embodiments, exhaust 514 includes one or more features to direct a direction of exhaust airflow. For example, exhaust 514 may include one or more adjustable fins to control a direction of exhaust air.

Display 516 may include one or more display elements such as LEDs that may display information associated with thermal adjustment device 500 (e.g., a battery level, a cooling/heating mode, a temperature setpoint, etc.). For example, in response to a user selecting a low cooling/heating mode, display 516 displays a first indication (e.g., illuminates a single blue/red LED, etc.). As another example, in response to a user selecting a medium cooling/heating mode, display 516 displays a second indication (e.g., illuminates two blue/red LEDs, etc.) As yet another example, in response to a user selecting a high cooling/heating mode, display 516 displays a third indication (e.g., illuminating three blue/red LEDs, etc.). In some embodiments, the LEDs include red-green-blue (RGB) LEDs. In various embodiments, display 516 includes a transparent (or semitransparent) portion of body 510 that facilitates light from one or more LEDs positioned within body 510 to be visible to a user. For example, thermal adjustment device 500 may include an array of internal LEDs and a light guide that may direct light from the LEDs to a portion of body 510 corresponding to display 516.

Input/output 518 may include an interface such as a USB type C connection to facilitate charging thermal adjustment device 500. In various embodiments, display 516 updates based on a charging/battery status. For example, display 516 may blink a number (e.g., three, etc.) of LEDs for a time period (e.g., five seconds, etc.) to indicate that a battery is empty. In some embodiments, display 516 flashes a first LED to indicate very low charge. In some embodiments, display 516 illuminates a first LED and flashes a second LED to indicate low/medium charge. In some embodiments, display 516 illuminates a first and second LED and flashes a third LED to indicate medium/high charge. In some embodiments, display 516 illuminates a first, second, and third LED to indicate full charge. In some embodiments, after indicating full charge, display 516 may turn off (e.g., turn off the first, second, and third LEDs, etc.). User interface 520 may facilitate user operation of thermal adjustment device 500. In some embodiments, user interface 520 includes first button 522, second button 524, and/or switch 526. First button 522 may increase a heating/cooling mode (e.g., heating/cooling intensity, etc.). For example, a user may press first button 522 to increase a heating mode from low to medium. Second button 524 may decrease a heating/cooling mode (e.g., heating/cooling intensity, etc.). For example, a user may press second button 524 to decrease a heating mode from high to medium. Switch 526 may facilitate selecting different modes (e.g., heating mode, cooling mode, off, etc.). In various embodiments, switch 526 includes a number of positions (e.g., three positions, etc.). For example, a user may move switch 526 from a first position to a second position to change thermal adjustment device 500 from an off mode to a cooling mode (e.g., turn on thermal adjustment device 500, etc.).

Fastener(s) 530 may include a screw, bolt, snap fastener, magnetic fastener, and/or any other mechanical fastener. Additionally or alternatively, fastener(s) 530 may include a tongue-and-groove fastener. For example, components of thermal adjustment device 500 (e.g., portions of a case of thermal adjustment device 500, etc.) may be fastened using a combination of screws and tongue-and-groove fasteners. Advantageously, the combination may provide increased structural strength compared with other fastening methods (e.g., a snap-fit construction, etc.). In some embodiments, fastener(s) 530 include one or more adhesives. For example, one or more components of thermal adjustment device 500 may be fastened using adhesive tape.

Figure 5I:
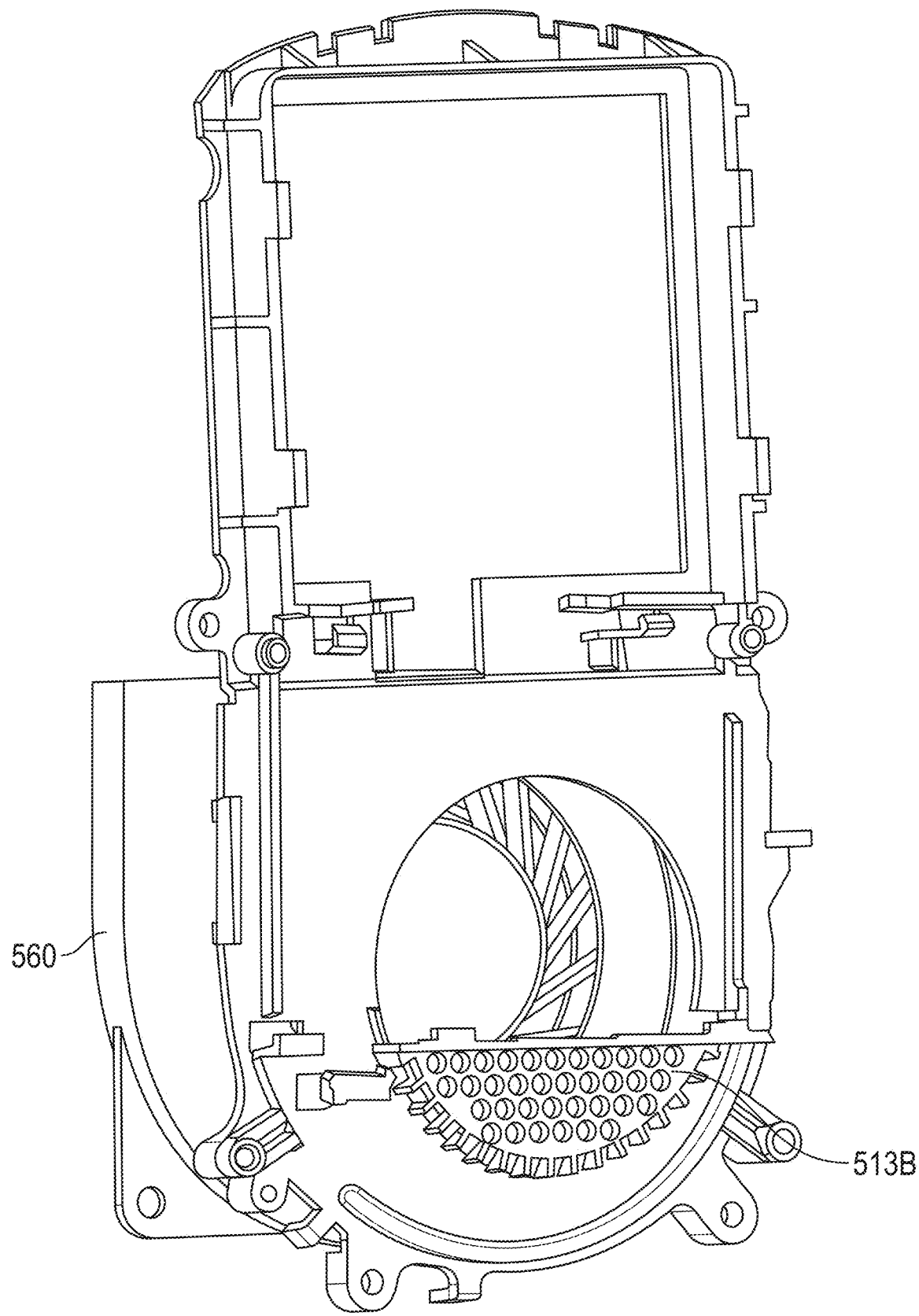
FIG. 5I illustrates an exemplary protective feature of an intake of a thermal adjustment device, in accordance with an embodiment.

FIG. 5I illustrates an exemplary protective feature of an intake of thermal adjustment device 500, in accordance with an embodiment. As discussed above, intake 512 may include second protective feature 513B to prevent a user's hair (or other particulate) from entering into thermal adjustment device and contacting fan 560. In various embodiments, second protective feature 513B includes a number of holes that restrict particulate ingress while allowing airflow to fan 560. Second protective features 513B may be offset from first protective feature 513A (e.g., offsetting the holes from the slits, etc.), thereby creating a barrier to particulate ingress (e.g., making it difficult for hair to ingress into intake 512, etc.).

Figure 6A:
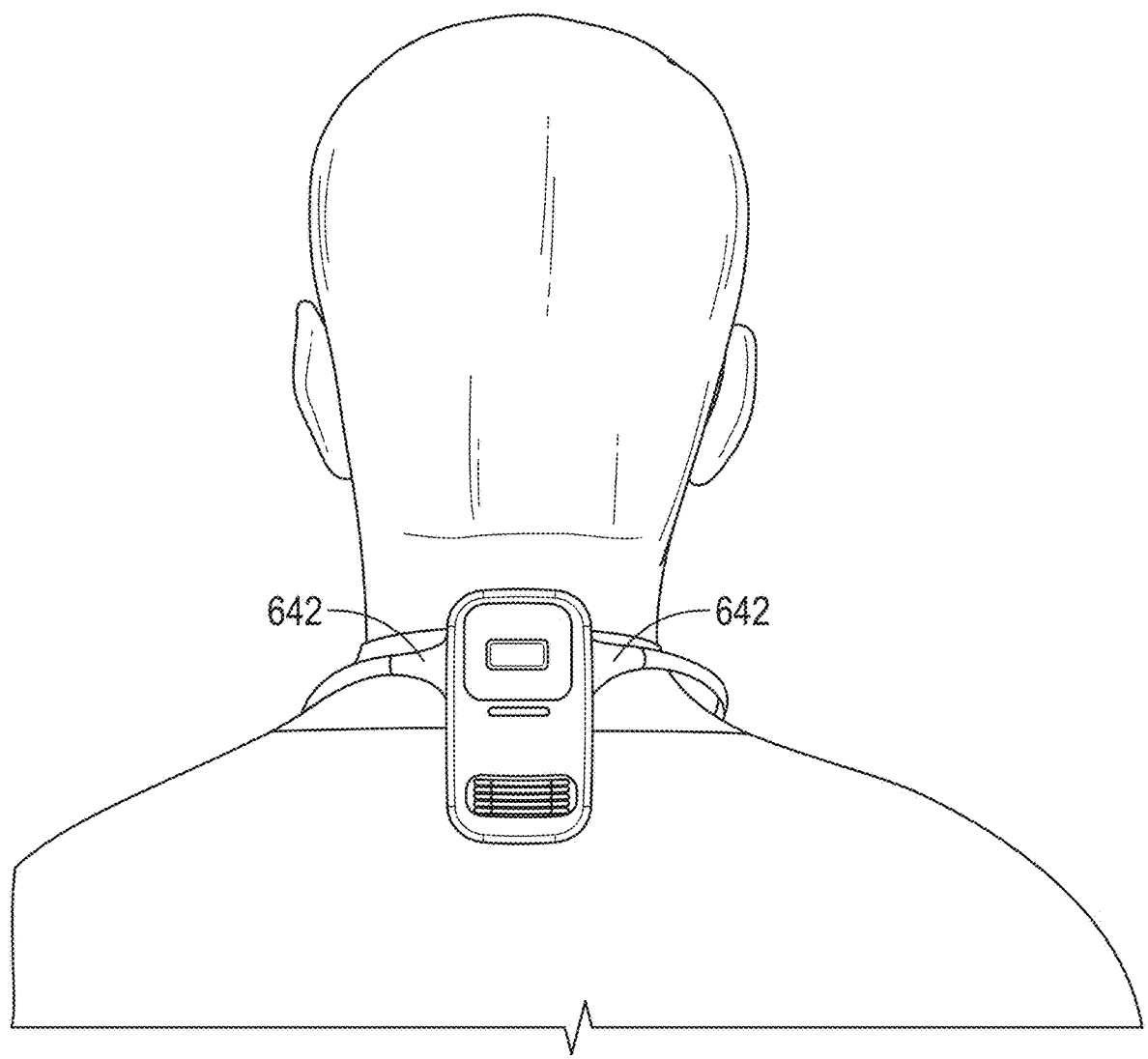
FIG. 6A-6D illustrates an exemplary thermal adjustment device as worn by a user, in accordance with an embodiment.
Figure 6B:
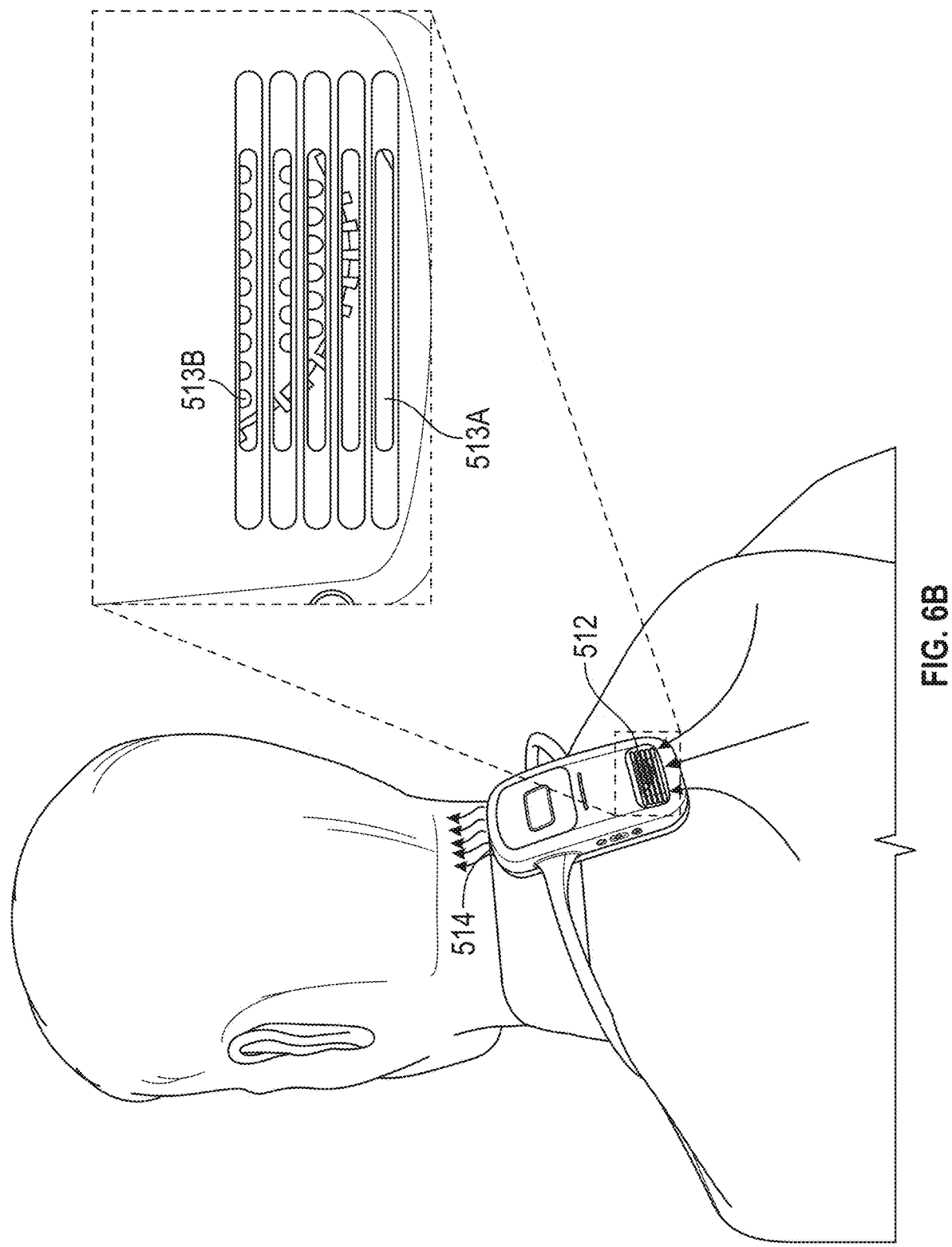
Figure 6C:
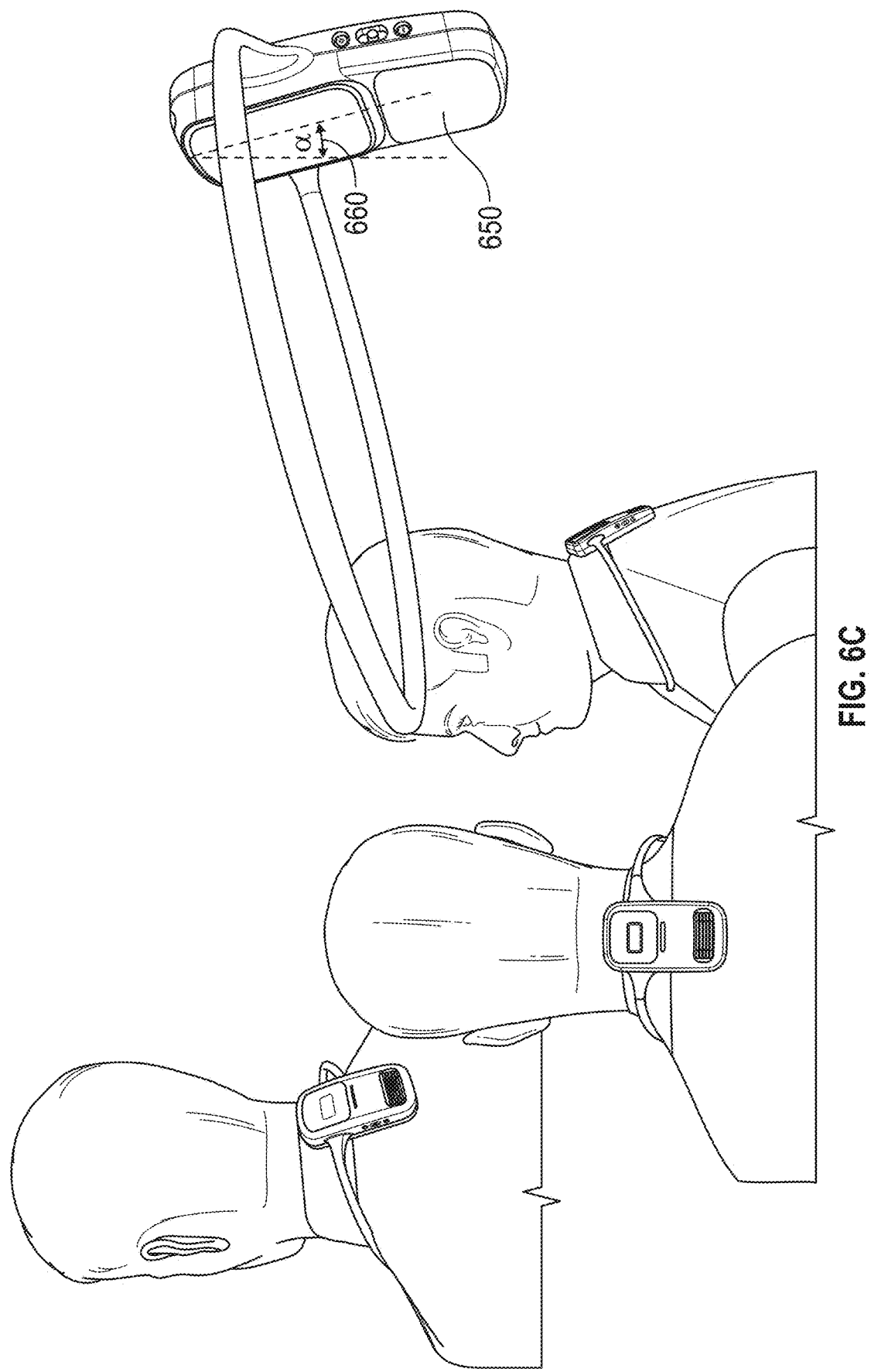

FIG. 6A-6C illustrates an exemplary thermal adjustment device 500 worn by a user, in accordance with an embodiment. In some embodiments, lanyard 600 is comprised of materials having different durability ratings. For example, pocket 630, in some embodiments, is constructed of silicon rubber Shore A30, but truss 642 (shown in FIG. 6A) is composed of Shore A60 durometer. The different materials may have different physical characteristics (e.g., stiffness, etc.). This configuration may advantageously provide additional structural support and flexibility, while increasing the device's resistance to impact. Multiple durometer ratings can be used. In some embodiments, the durometer ranges from 30 to 60. In some embodiments, truss 642 provides stiffness to reduce force on the user's throat when wearing.

In some embodiments, openings on lanyard 600 (shown as first aperture 612 and second aperture 614, respectively) for intake and exhaust of thermal adjustment device 500 (e.g., shown as intake 512 and exhaust 514, respectively) are placed to align with venting (e.g., shown as exhaust 514). A cooling mode is illustrated in FIG. 6B, with an ambient blue intake 512 and red warm exhaust 514. In various embodiments, intake 512 and/or exhaust 514 include structural features to prevent an ingress of particulate matter and/or hair. For example, intake 512 may include a first set of horizontal slits (shown as first protective feature 513A) and a second set of holes (shown as second protective feature 513B) to prevent ingress of a user's hair into thermal adjustment device 500. In various embodiments, first aperture 513A and second aperture 513B are offset, thereby reducing a possibility of particulate ingress. FIG. 6C illustrates an advantageous placement of thermal adjustment device 500 under a shirt and directly contacting the user's skin. In some embodiments, a silicon rubber contact patch (illustrated under the thermal skin-contact surface, shown as contact portion 650) increases the coefficient of friction of the device and thereby reduces movement of thermal adjustment device 500 and/or lanyard 600 by contact with skin (or another surface such as an undershirt). In some embodiments, body 510 forms angle 660 with the user's upper back. In some embodiments, angle 660 ranges from 0-35 degrees. Advantageously, angle 660 may increase a contact force between thermal adjustment device 500 and/or lanyard 600 and a user's skin (or other contact surface such as an undershirt, etc.), thereby reducing movement of thermal adjustment device 500 and/or lanyard 600.

Figure 6D:
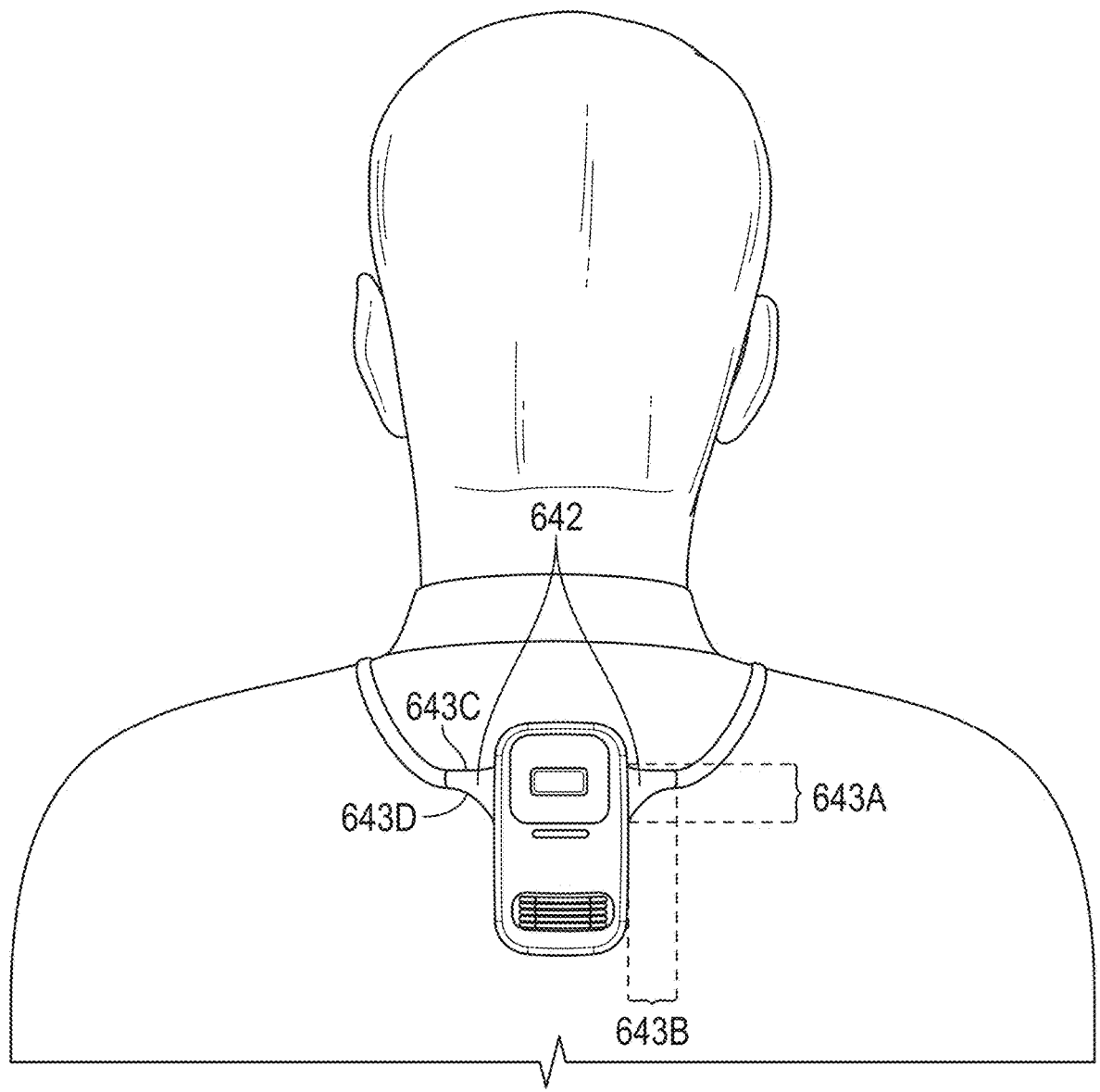

FIG. 6D illustrates exemplary trusses 642 of lanyard 600, in accordance with an embodiment. Trusses 642 may include first dimension 643A (e.g., a height) and second dimension 643B (e.g., a width). First dimension 643A may range from 10 mm-30 mm Second dimension 643B may range from 15 mm-30 mm. In various embodiments, trusses 642 are constructed of a material having a stiffness sufficient to prevent/reduce mechanical deformation (e.g., bending, twisting, etc.). For example, trusses 642 may reduce a deformation of arms 640 away from a user's back, thereby facilitating secure contact between a heat conducting surface of thermal adjustment device 500 and a user's skin. Advantageously, by preventing/reducing mechanical deformation, trusses 642 may broaden a contact area on a neck/shoulders of a user and thereby reduce pressure (e.g., of arms 640, etc.) on a throat area of a user. For example, trusses 642 may change a point of deformation of arms 640 such that a load of lanyard 600 is distributed on a user's shoulders. In some embodiments, the point of deformation is 25 mm-35 mm (e.g., measured along second dimension 643B from a point where arms 640 contact a body of lanyard 600, etc.). In various embodiments, first portion 643C of trusses 642 is in mechanical compression while second portion 643D of trusses 642 is in mechanical tension. In various embodiments, trusses 642 couple to a body of lanyard 600 above a center of gravity of thermal adjustment device 500 when inserted into lanyard 600, thereby reducing deformation of arms 640 away from a user's back.

Figure 7:
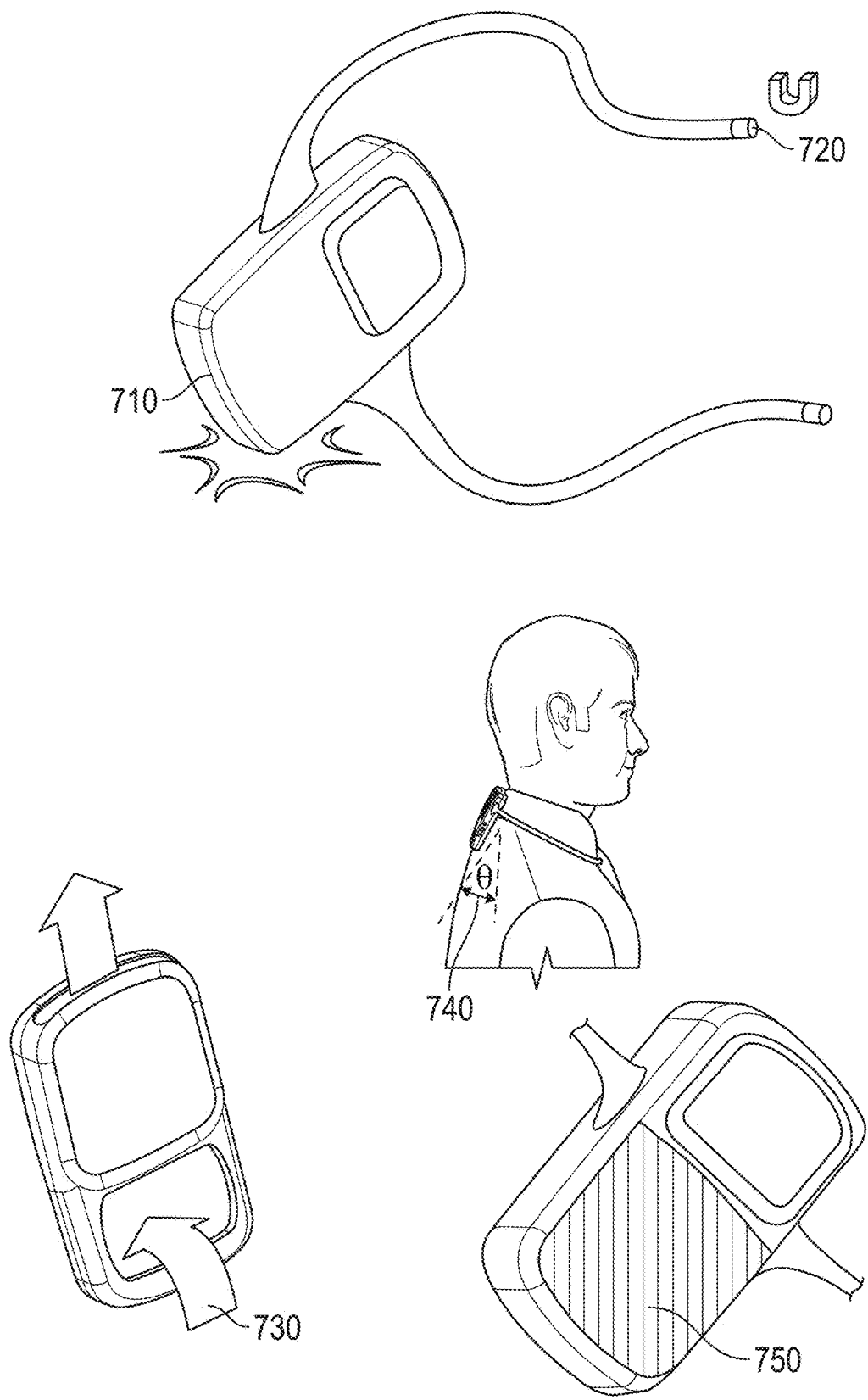
FIG. 7 illustrates an exemplary thermal adjustment device and corresponding features, in accordance with an embodiment.

FIG. 7 illustrates an exemplary thermal adjustment device 500 and corresponding features, in accordance with an embodiment. As shown, thermal adjustment device 500 may include lanyard 600 that is configured to insulate a surface of thermal adjustment device 500 from a user's skin. As describe above, lanyard 600 may provide impact resistance (shown as impact resistance 710) for thermal adjustment device 500. Lanyard 600 may include one or more of fastener 644 to facilitate coupling/uncoupling thermal adjustment device 500 and/or lanyard 600 with a user (e.g., by securing lanyard 600 around a neck/shoulder region of a user, etc.). Fastener 644 may include a snap fastener, a magnetic fastener (shown as magnetic fastener 720), a clip, and/or the like. Lanyard 600 may be positioned at a non-zero angle relative to a vertical surface of a user's body (shown as angle 740) such that lanyard 600 reduces movement of lanyard 600 and/or thermal adjustment device 500 relative to a surface (e.g., a user's skin, etc.). Lanyard 600 may include a contact portion (shown as non-slip portion 750) that may increase a coefficient of friction between a user's skin and thermal adjustment device 500/lanyard 600, thereby facilitating a secure fit of thermal adjustment device 500 against a user's skin. Lanyard 600 may include one or more air vents (shown as first aperture 612 and second aperture 614 in FIG. 5G above) to facilitate airflow (shown as airflow 730) to thermal adjustment device 500.

Figure 8A:
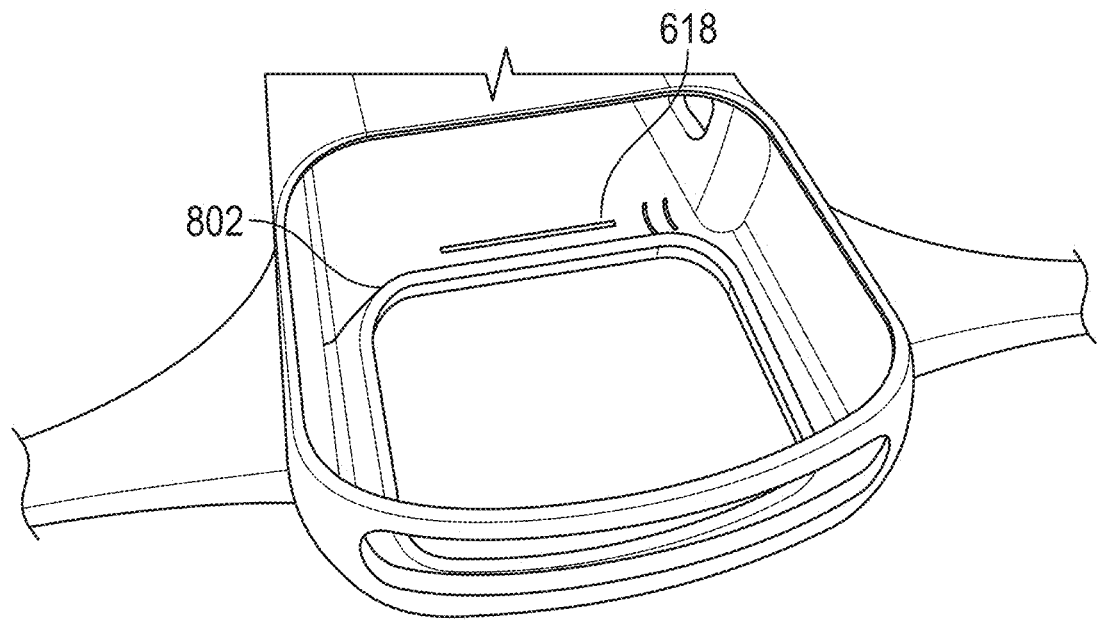
FIGS. 8A-8C illustrates an exemplary method of manufacturing an exemplary lanyard of a thermal adjustment device, in accordance with an embodiment.
Figure 8B:
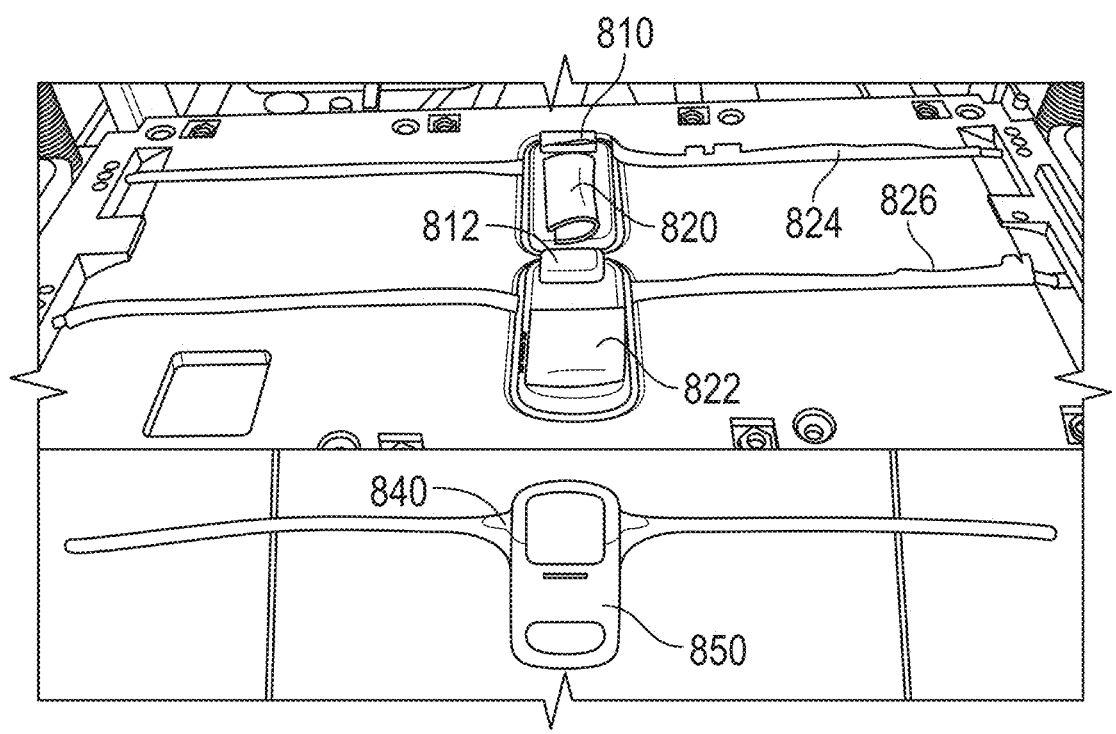
Figure 8C:
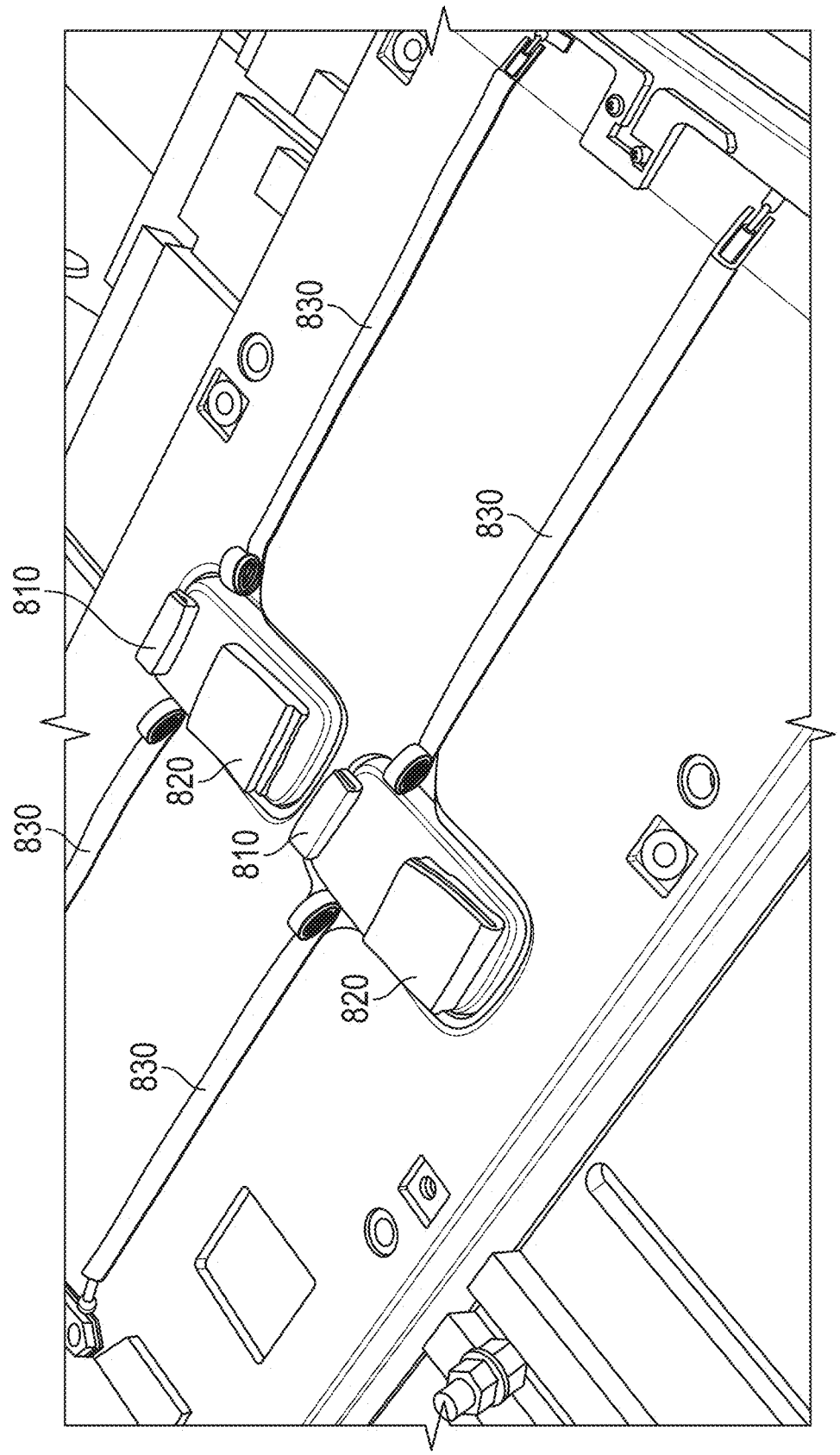

FIG. 8A-8C illustrates an exemplary method of manufacturing an exemplary lanyard 600 of thermal adjustment device 500, in accordance with an embodiment. In the exemplary embodiment of FIGS. 8A-8C, raw material (for example, the red silicon could be Silicon Rubber Shore A60, while the white silicon could be Silicon Rubber Shore A45) placed to produce the advantageous increase in structural support and flexibility, while also increasing the device's resistance to impact. The different colors are for illustrative purposes. As shown in FIG. 8A, a number of pieces of raw material (shown as first material 810, second material 812, third material 820, fourth material 822, fifth material 824, and sixth material 826) may be formed/combined into first composite material 840 and second composite material 850. In some embodiments, first composite material 840 includes Silicon Rubber Shore A 70. In some embodiments, second composite material 850 includes Silicon Rubber Shore A 45. In some embodiments, materials 810-812 are the same (e.g., Silicon Rubber Shore A 60, Silicon Rubber Shore A 70, etc.). In some embodiments, materials 820-826 are the same (e.g., Silicon Rubber Shore A 45). In various embodiments, a material having a first durometer value (e.g., stiffness, etc.) is used for a first portion of lanyard 600 and a material having a second durometer value is used for a second portion of lanyard 600. For example, as shown in FIG. 8B, first composite material 840 may be used along a top portion of lanyard 600 to connect between trusses 642 while second composite material 850 is used for the rest of lanyard 600, thereby providing increased rigidity along a top portion of lanyard 600 such that lanyard 600 is suitably positioned against a user's back during use. As another example, Silicon Rubber Shore A 70 is used to create first composite material 840 and Silicon Rubber Shore A 45 is used to create second composite material 850.

FIG. 8C illustrates another method of manufacturing using the same color for raw material of different strength. As shown, a number of pieces of raw material (shown as first material 810, third material 820, and seventh material 830) may be positioned to form a composite component (e.g., lanyard 600, etc.). In some embodiments, first material 810 has a first durometer value that is greater than (e.g., stiffer than, etc.) a second durometer value of third material 820 and/or seventh material 830.

Generally, as used herein, the term "substantially" is used to describe element(s) or quantit(ies) ideally having an exact quality (e.g., fixed, the same, uniformed, equal, similar, proportional), but practically having qualities functionally equivalent to the exact quality. For example, an element or quantity is described as being substantially fixed or uniformed can deviate from the fixed or uniformed value, as long as the deviation is within a tolerance of the system (e.g., accuracy requirements, etc.). As another example, two elements or quantities described as being substantially equal can be approximately equal, as long as the difference is within a tolerance that does not functionally affect a system's operation.

Likewise, although some elements or quantities are described in an absolute sense without the term "substantially", it is understood that these elements and quantities can have qualities that are functionally equivalent to the absolute descriptions. For example, in some embodiments, a ratio is described as being one. However, it is understood that the ratio can be greater or less than one, as long as the ratio is within a tolerance of the system (e.g., accuracy requirements, etc.).

Although the disclosed embodiments have been fully described with reference to the accompanying drawings, it is to be noted that various changes and modifications will become apparent to those skilled in the art. Such changes and modifications are to be understood as being included within the scope of the disclosed embodiments as defined by the appended claims.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

What is claimed is:

1. A method for controlling the temperature of a surface using a thermal adjustment device, the method comprising:
    applying a variable input to a heat pump of the thermal adjustment device in thermal communication with the surface;
    measuring, by the thermal adjustment device, a temperature of an element in thermal communication with the surface;
    determining, by the thermal adjustment device based on the temperature of the element, whether a temperature of the surface is within a safe temperature range for a user in thermal communication with the surface;
    in response to determining the surface is not within the safe temperature range, adjusting, by the thermal adjustment device, a voltage of the variable input to the heat pump; and
    in response to determining the surface is within the safe temperature range, continuing, by the thermal adjustment device, operation of the variable input at the voltage, wherein:
    the heat pump is configured to operate in at least a first mode and a second mode,
    when the heat pump operates in the first mode, the safe temperature range comprises a first temperature range, and
    when the heat pump operates in the second mode, the safe temperature range comprises a second temperature range different from the first temperature range.

2. The method of claim 1, wherein the safe temperature range for the user is between 15 degrees Centigrade and 50 degrees Centigrade.

3. The method of claim 1, wherein a duty cycle of the variable input is at least 10%.

4. The method of claim 1, wherein the voltage of the variable input is within a safe operating range for the heat pump.

5. The method of claim 1, wherein each of the first mode and the second mode comprises two stages, and wherein each stage of the two stages is associated with a different duration.

6. The method of claim 1, wherein adjusting the voltage of the variable input comprises reducing an amount of power provided to the heat pump.

7. The method of claim 1, further comprising adjusting operation of a fan based on the temperature of the element.

8. The method of claim 1, wherein the variable input comprises a powered period and an unpowered period.

9. The method of claim 8, wherein a duration of the powered period is greater than a duration of the unpowered period.

10. The method of claim 1, wherein the heat pump comprises a Peltier.

\* \* \* \* \*